(12) United States Patent
Rait

(10) Patent No.: US 10,774,358 B2
(45) Date of Patent: Sep. 15, 2020

(54) METHOD FOR INCREASING AVAILABLE PROTEIN FROM ENDOSPORES FOR DETECTION PURPOSES

(71) Applicant: 20/20 GeneSystems Inc., Rockville, MD (US)

(72) Inventor: Vladimir Rait, Rockville, MD (US)

(73) Assignee: 2020 GeneSystems Inc., Rockville, MD (US)

(*) Notice: Subject to any disclaimer, the term of this patent is extended or adjusted under 35 U.S.C. 154(b) by 183 days.

(21) Appl. No.: 15/772,088

(22) PCT Filed: Oct. 29, 2016

(86) PCT No.: PCT/US2016/059609
§ 371 (c)(1),
(2) Date: Apr. 29, 2018

(87) PCT Pub. No.: WO2017/075552
PCT Pub. Date: May 4, 2017

(65) Prior Publication Data
US 2018/0312896 A1 Nov. 1, 2018

Related U.S. Application Data

(60) Provisional application No. 62/248,352, filed on Oct. 30, 2015.

(51) Int. Cl.
| | | |
|---|---|---|
| *C12Q 1/04* | (2006.01) | |
| *C12N 3/00* | (2006.01) | |
| *G01N 33/52* | (2006.01) | |
| *G01N 33/68* | (2006.01) | |
| *C07H 21/00* | (2006.01) | |
| *C12Q 1/24* | (2006.01) | |
| *C12Q 1/68* | (2018.01) | |
| *G01N 15/10* | (2006.01) | |
| *G01N 33/552* | (2006.01) | |

(52) U.S. Cl.
CPC ............... *C12Q 1/04* (2013.01); *C07H 21/00* (2013.01); *C12N 3/00* (2013.01); *C12Q 1/24* (2013.01); *C12Q 1/68* (2013.01); *G01N 15/10* (2013.01); *G01N 33/52* (2013.01); *G01N 33/552* (2013.01); *G01N 33/6803* (2013.01); *G01N 33/6839* (2013.01); *G01N 2015/1087* (2013.01)

(58) Field of Classification Search
None
See application file for complete search history.

(56) References Cited

U.S. PATENT DOCUMENTS 6,828,110 B2 * 12/2004 Lee ................. C07K 14/32
424/246.1

FOREIGN PATENT DOCUMENTS

WO WO-2013117968 A1 * 8/2013 ............... C12N 1/06

* cited by examiner

*Primary Examiner* — Heidi Reese
(74) *Attorney, Agent, or Firm* — Koren Anderson

(57) ABSTRACT

Methods, kits and reagents are provided for increasing the sensitivity of detecting the presence or absence of endospores by increasing the available protein for detection. The methods are fast and amendable to testing in a non-laboratory setting and use a protein detection reagent and solid microparticles.

20 Claims, 23 Drawing Sheets

1 and 2 – 250 μg of a corn starch before and after 30-sec beating with 300 mg beads;
3 and 4 – 250 μg of *B. cereus* spores before and after 30-sec beating with 300 mg beads.

METHOD FOR INCREASING AVAILABLE PROTEIN FROM ENDOSPORES FOR DETECTION PURPOSES

CROSS-REFERENCE TO RELATED APPLICATIONS

This application claims the benefit of U.S. Provisional Patent Application No. 62/248,352, filed on 30 Oct. 2015, the contents of which are incorporated herein by reference in its entirety.

FIELD OF THE INVENTION

The disclosure relates to methods and kits for processing of dry powder for protein analysis and detection of bacterial spores.

BACKGROUND

There is a continuing need to be able to detect and identify bacterial spores. For example in the food industry there is a desire for rapid analysis of food stuffs to detect the presence of any bacterial spores, such as Bacillus cereus, before they can germinate and spoil produce and/or cause illness. Equally there is a need for rapid detection/identification of spores used as biowarfare agents such as Bacillus anthracis.

Current methods for detection of spores include germination via heat activation and outgrowth. However this process takes up to 48 hours and requires skilled personnel and therefore is unsuitable for rapid in the field identification.

More rapid tests exploit antibodies associated to the surface of the spores (exosporium) for detection. Handheld immunochromatographic tests are available but the sensitivity of such test are low.

Likewise, non-specific protein detection agents used for exosporium detection suffer from the same shortcoming; low sensitivity.

Sonication may also he used to modify the surface of spores so as to aid subsequent detection of spore protein via an immunoassay or non-specific protein reagents. Detection sensitivity can be improved by modification of the surface of the species to be detected so as to improve subsequent binding to the antibodies on the biosensor.

Another method of screening for spores is to completely disrupt the spore so as to release intrasporal DNA for subsequent analysis via polymerase chain reaction (PCR) assays. For instance ultrasonication has been proposed to completely disrupt spores in 'Belgrader P.; Hansford D.; Kovacs G. T. A.; Venkateswaran, K; Mariella, R.; Milanovich, F.; Nasarabadi, s.; Okuzumi, m; Pourahmadi, F.; Northrup, M. A. *Analytical Chemistry* 1999, 71, 4232-4236'. However the samples can require pretreatments of up to 90 minutes and so far the amount of intrasporal DNA released has been low so the technique would not currently be sensitive enough for most applications.

In the case of Anthrax (*Bacillus anthracis*), treatment is effective if initiated within 72 hours of infection. This means that samples must be analyzed in time to identify potentially infected individuals and begin treatment. However, because the effects of exposure to anthrax are not immediate, and because the initial symptoms are easily confused with the flu, there is a need for a fast method to detect *B. anthracis* in an environment where *B. anthracis* may have been released. This need is enhanced by the increasing number of anthrax threats that are called into governmental authorities each year. A fast sensitive method for determining whether public places have been exposed to anthrax spores is therefore essential.

Therefore, there is a need for a method that increases the availability of intrasporal protein for detection, and thus increases sensitivity, that is rapid and amenable to testing outside of a laboratory setting.

SUMMARY

Provided herein are methods, kits and reagents for increasing the sensitivity for detecting bacterial spores (e.g. dormant endospores) in a sample by increasing the exposed protein available for detection. In certain embodiments, is provided a method for detecting the presence of dry bacterial spores using a protein detection reagent and solid microparticles, comprising collecting a sample suspected of comprising dry bacterial spores, contacting the solid microparticles with the collected dry bacterial spores, applying a mechanical force sufficient to break open the spores to increase exposed protein; and, contacting the dry bacterial spores, either before breaking open or after, to at least one reagent that produces color in the presence of protein, wherein a color change indicates the presence of protein and the suspected dry bacterial spores in the sample. In certain embodiments, the bacterial spores, after mechanical disruption, are contacted with the protein detection reagent. In alternative embodiments, the dry bacterial spores are contacted with the protein detection reagent before the bacterial spores are subjected to mechanical force with the solid particles.

In embodiments, the sample is dry powder. In embodiments, the sample suspected of comprising dry bacterial spores is a biowarfare agent that may comprise *Bacillus anthracis* or *Clostridium botulinum*. In other embodiments, the bacterial spores are pathogenic and may comprise *Bacillus* spores or *Clostridium* spores. In embodiments, the sample suspected of comprising dry bacterial spores may comprise *Bacillus cereus* or *Bacillus anthracis* spores.

In embodiments, the solid microparticles comprise glass or zirconia/silica beads. In embodiments, the solid microparticles have a diameter a diameter from about 5 to about 500 µm or a diameter of about 100 µm.

In embodiments, collecting the sample comprises using an absorbent pad or swab. In embodiments, the at least one detection reagent is colorimetric reagent, such as those used in a BCA protein assay, Lowry protein assay or Coomassie protein assay. In embodiments, the protein detection reagent is bicinchoninic acid (BCA), a mixture of phosphotungstic acid and phosphomolybdic acid, or Coomassie blue dye.

In embodiments, the step of applying a mechanical force sufficient to break open the spores to increase available protein improves the detection of protein in the sample as compared to methods in the absence of that step and use of solid microparticles. In embodiments, the improvement is a 5× increase in sensitivity of protein detection.

In embodiments, provided herein are kits for the detecting the present of dry bacterial spores using a protein detection reagent and solid microparticles, comprising at least one aliquot of solid microparticles, a sample collection device, at least one sample tube for bead milling and optionally a protein detection reagent. The kit may further comprise an aliquot of the solid microparticles in a microfuge tube; a mini scoop for sample collection; a pre-wetted swab with a solution of copper sulfate and a tube comprising a bicinchoninic acid solution. In embodiments, the kit may further comprise a battery powered vortex. In embodiments, the kits comprise a detection reagent selected from bicinchoninic acid (BCA), a mixture of phosphotungstic acid and phosphomolybdic acid, and Coomassie blue dye.

BRIEF DESCRIPTION OF THE DRAWINGS

The accompanying drawings, which are incorporated into and constitute a part of this specification, illustrate one or more embodiments of the present disclosure and, together with the detailed description and examples sections, serve to explain the principles and implementations of the disclosure.

FIGS. 11-14 utilize a vortex to mechanically disrupt the endospores with milling beads. FIGS. 15-17 depict the use of an OmniLyse Disruptor from Claremont BioSolutions (J. Clinical Microbiology, July 2011 p. 2533-2539).

DETAILED DESCRIPTION

A) Introduction

The present disclosure provides methods for processing dry powder for protein analysis. Provided herein are methods and compositions for detecting the presence of dry bacterial spores using a protein detection reagent and solid (micro)particles. In embodiments, the present invention is used as part of a test for biowarfare agents in triaging possible contaminated sites. Additional applications include testing food stuff, such as produce.

Figure 1:
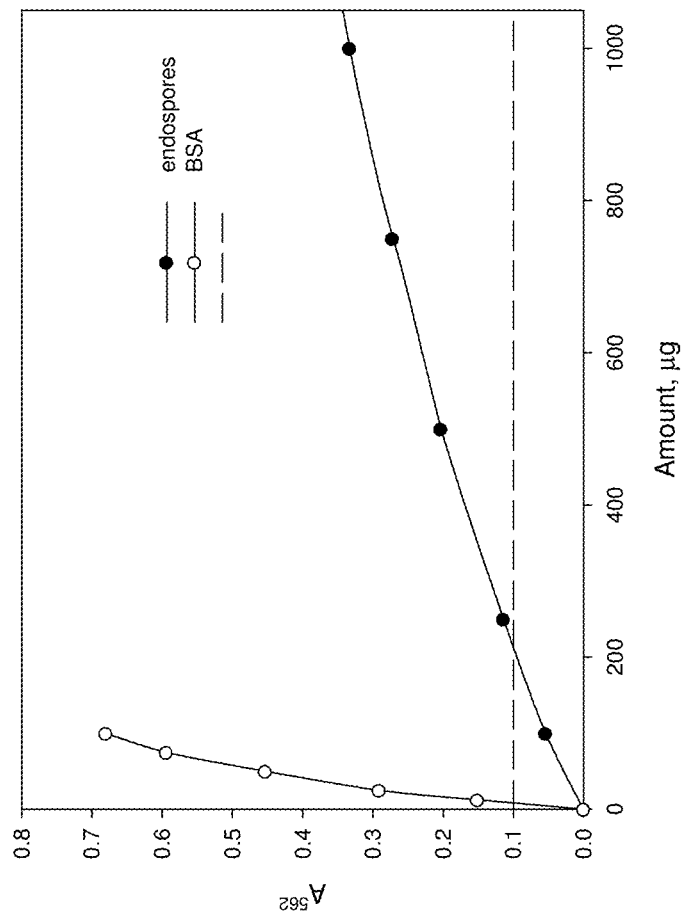
FIG. 1 Shows the limits of detection (LOD) for endospore proteins compared to BSA at 70° C. using the BCA protein detection assay.
Figure 2:
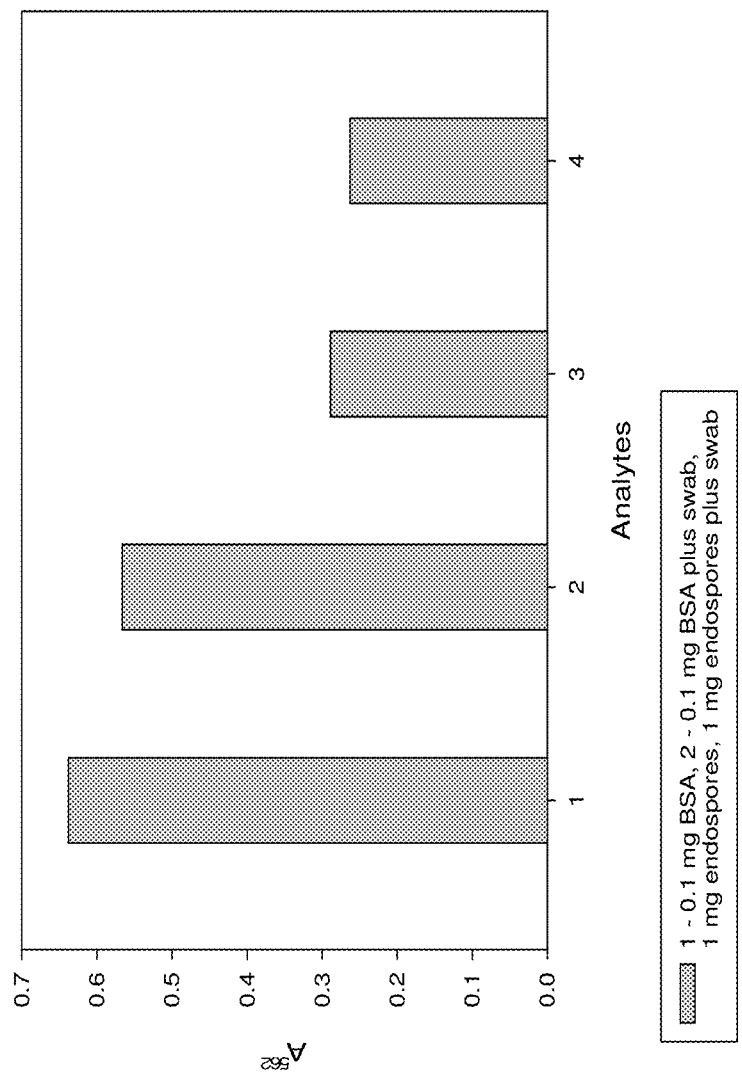
FIG. 2 Shows the detection of endospore protein and BSA with and without using a swab for sample collection.

In embodiments, the sample suspected of comprising dry bacterial spores (e.g. endospores) is collected and subjected to a process that breaks open the spores using solid particles, also referred to herein as milling beads or solid microparticles, and a mechanical force. The beads may be used with the dry bacterial spores or after the spores have been contacted with an aqueous solution such as the protein detection reagents; a mechanical force is applied to the sample and beads to disrupt or break open the endospores. This process exposes a larger amount of protein to the protein detection reagents by releasing intrasporal protein as well increasing available coat proteins, and thus lowers the limit of detection (from about 212 µg (FIG. 1) to about 28-29 µg (FIG. 5)) for bacterial endospores when using colorimetric detection. The invention provides for a rapid and convenient method to perform preliminary analysis of a suspected sample with an improved degree of sensitivity for endospore protein than possible without mechanical lysing of the spores.

Others have developed methods for protein extraction from sporulated *Bacillus* species (e.g. *B. anthracis, B. cereus, B. thuringiensis*, and *B. subtilis*). Other assays include: 1) 1. Microwave 90-s irradiation of a spore suspension (1 mg/ml) in 6% formic acid (Anal. Chem. 2006, 78, 181-188); 2) Heating for 15 min at 90° C. in 2 M thiourea and 2% 2-mercaptoethanol in 50 mM Tris-HCl, pH 10 (Appl. Environ. Microbiol. 2006, 72, 6355-6363); 3) Two 30-s bursts of agitation in 50 mM Tris-HCl, 0.5 mM EDTA, and 1 mM PMSF using a FastPrep cell disintegrator and breakage beads (J. Bacteriol. 2001, 183, 4317-4322); 4) A 15-min incubation in 2% SDS, 2-min boiling in a water bath, and 5-min sonication (Appl. Environ. Microbiol. 2008, 74, 904-906); and 5) A 8-min boiling in 125 mM Tris-HCl, 4% SDS, 10% 2-mercaptoethanol, 1 mM DTT, 0.05% Bromophenol blue, 10% glycerol, pH 6.8 (Methods 2000, 20, 95-110).

However, each of those methods are either unsatisfactory for non-laboratory settings or they contain chemicals that are either known to or may interfere with protein detection reagents, such as those used in the bicinchoninic acid assay (BCA) protein detection assay. The present method utilizes only solid particles and mechanical force to break open the spores, and therefore additional chemicals are avoided that may interfere with a protein detection assay.

In embodiments are provided methods for detecting bacterial spores in the field utilizing colorimetric protein detection reagents. In the field refers to a non-laboratory setting without the requirement for A/C power or the need to take a sample back to a laboratory. In illustrative embodiments provided herein are methods for detecting bacterial spores in the field utilizing BCA reagents (Reagent A (bicinchoninic acid solution) and B (copper(II) sulfate solution)), wherein a suspicious sample is collected and placed in a tube (such as a microfuge tube) containing an aliquot of dry milling beads, the sample in the tube is then subjected to a mechanical force "bead milling" (such as vortexing with a batter powered vortex), the bead milled sample is transferred to another tube either containing a BCA reagent (e.g. Reagent A; bicinchoninic acid solution) or it is added shortly after transfer of the bead milled sample, Reagent B (copper(II) sulfate solution) is then added to the tube (such as in the form of a pre-wetted swab), the sample is then gently mixed, incubated and color change observed. In embodiments, the transfer of the bead milled sample is accomplished by pouring. In other embodiments, a pre-wetted swab with BCA Reagent B is used to transfer the sample and in certain further embodiments the sample is transferred with a combination of pouring and the pre-wetted swab.

The process results in a significant increase in detection of intrasporal protein as compared to a process that does not utilize bead milling. See FIG. 23 and Example 7.

B) Definitions

As used herein, the terms "a" or "an" are used, as is common in patent documents, to include one or more than one, independent of any other instances or usages of "at least one" or "one or more."

As used herein, the term "or" is used to refer to a nonexclusive or, such that "A or B" includes "A but not B," "B but not A," and "A and B," unless otherwise indicated.

As used herein, the term "about" is used to refer to an amount that is approximately, nearly, almost, or in the vicinity of being equal to or is equal to a stated amount, e.g., the state amount plus/minus about 5%, about 4%, about 3%, about 2% or about 1%.

As used herein, the term "bacteria" refers to single-cell prokaryotic microorganism species typically of a few micrometers in length and a wide range of shapes, including but not limited to Gram-negative bacteria and Gram-positive bacteria. The term "Gram-negative bacteria" refers to bacterial species that do not retain crystal violet dye in the Gram staining protocol. In contrast, the wording "Gram-positive bacteria" refers to bacterial species that are stained dark blue or violet by Gram staining. Several Gram-positive bacteria form endospores, including but not limited to the genus *Bacillus* and *Clostridium*. *Bacillus* bacteria are rod-shaped, aerobic or facultative, endospore-forming bacteria. The spores of *Bacillus* are particularly hard to lyse by either physical or chemical means due to its structure and composition. A spore core is surrounded by the core wall, a cortex and a spore coat.

As used herein, the term "bacterial endospore" indicates a dormant and temporarily non-reproductive structure produced by certain bacteria, the formation of which is usually triggered under an unfavorable condition for bacteria, such as a lack of nutrients. The endospore typically consists of the bacterium's DNA and part of the bacterium cytoplasm, surrounded by a very tough outer coating, known as the endospore coat. Generally, when the environment becomes more favorable, the endospore can germinate to the metabolically active state, known as the vegetative state. Examples of bacteria able to form endospores comprise bacteria of the genus *Bacillus* and *Clostridium*. As used herein, "endospore" and "spore" as used interchangeably.

For example, bacterial spores (endospores) produced by the genera *Bacillus* and *Clostridium* are a dormant form of cells that can persist for a long time in harsh conditions without dividing and display resistance towards chemical disinfectants, UV- and γ-radiation, and extreme pH, temperature, pressure and dryness. These dormant spores are capable of passively monitoring the surrounding environmental conditions, and germinating into physiologically active vegetative cells upon exposure to favorable situations. Several species of spore-forming bacteria are reported as pathogenic to humans and terrestrial and aquatic life and can survive hospital disinfection procedures.

As used herein, "biowarfare agent" refers to the use of biological toxins or infectious agents such as bacteria, viruses, and fungi with intent to kill or incapacitate humans, animals or plants as an act of war Examples of biowarfare agents or potential biowarfare agents include *Bacillus anthracic*, *Clostridium botulinum*, *Francisella tularensis*, *Burkholderia mallei*, *Burkholderia pseudomallei*, *Brucella* species, *Chlamydia psittaci*, *Corynebacterium diphtheriae*, *Coxiella burnettii*, *Cryptococcosis neofomans*, *Escherichia coli*, *Francisella tularensis*, *Haemophilus influenzae*, *Mycobacterium tuberculosis*, *Neiserria menigitidis*, *Rickettsia* species, *Salmonella* species, *Shigella* species, *Staphylococcus* species, *Streptococcus* species, *Vibrio cholerae*, and *Yersinia pestis*. Biowarfare agents can also include fungal pathogens that can be naturally present in an environment but that have been intentionally introduced as biowarfare agents. Examples include *Blastomyces dermatitidis*, *Coccidiodes immitis*, *Histoplasma capsulatum*, *Coccidioidomycosis* and *Nocarida* species.

As used herein, the terms "detect" or "detection" indicates the determination of the existence, presence or fact of a target in a limited portion of space, including but not limited to a sample, a reaction mixture, a molecular complex and a substrate. The "detect" or "detection" as used herein can comprise determination of chemical and/or biological properties of the target, including but not limited to ability to interact, and in particular bind, other compounds, ability to activate another compound and additional properties identifiable by a skilled person upon reading of the present disclosure. The detection can be quantitative or qualitative. A detection is "quantitative" when it refers, relates to, or involves the measurement of quantity or amount of the target or signal (also referred as 'quantitation'), which includes but is not limited to any analysis designed to determine the amounts or proportions of the target or signal. A detection is "qualitative" when it refers, relates to, or involves identification of a quality or kind of the target or signal in terms of relative abundance to another target or signal, which is not quantified.

As used herein, the term "intrasporal" protein refers to any protein not available on the surface of the spore for protein detection. In the present methods, available intrasporal protein refers to the protein that is exposed and available for detection using non-specific protein detection reagents following mechanical spore disruption with solid particles according to the present disclosure.

As used herein, the term "sample" indicates a limited quantity of something that is indicative of a larger quantity of that something, including but not limited to solids and/or fluids from a biological environment, specimen, cultures, tissues, commercial recombinant proteins, synthetic compounds or portions thereof. Exemplary samples in the sense of the current disclosure include an environment sample in the form of a dry powder collected from soil, air, surface of a facility, equipment or system, mail, such as a letter, equipment used to process mail and packages, surface of household items, food or pharmaceutical preparation.

As used herein, the term "spore" indicates a reproductive structure that is adapted for dispersal and surviving for extended periods of time in unfavorable conditions. Exemplary spores detectable with methods and systems herein described comprise spores from many bacteria, plants, algae, fungi and some protozoa. In some embodiments, detectable spores can be endospores. In general, spores comprise a protective protein-based coating which can comprise various spore proteins, forming a protein component of the spore coating. The protein component of a spore coating is typically comprised in more than one coating layers of the spore coating. In some embodiments, the spores are bacterial spores.

As used herein, the terms "solid microparticle" or "solid particle" refer to a microsphere or metal particle of appropriate size (e.g. 5-500 µm in diameter) and hardness that when used with mechanical force, such as a vortex, will break open an endospore. These solid microparticles may also be referred to herein as milling beads. There is no intended limitation on the shape of solid particles, provided they are capable of breaking open endospores and therefore increasing the amount of available protein for detection. Illustrative solid particles include zirconia/silica milling beads.

C) Method For Detecting the Presence of Dry Bacterial Spores Using a Protein Detection Reagent and Solid Microparticles In embodiments provided herein are methods for processing a sample suspected of comprising dry bacterial spores. In embodiments, the sample is a dry powder suspected of containing protein. In embodiments, the sample is a dry powder suspected of containing dry bacterial spores. In embodiments, the methods provide a process for increasing the amount of protein available for detection using standard protein detection methodology. In embodiments, the present methods use colorimetric protein detection methods and reagents. In embodiments, at least one regent that produces color in the presence of protein, wherein a color change indicates the presence of protein and the suspected dry bacterial spores in the sample, is used.

In embodiments, the present methods utilize solid particles and mechanical force to break apart dry bacterial cells such as endospores whereby availability of intrasporal protein and spore wall protein is increased. This protein is available for detection and therefore increases the sensitivity of a protein assay for detection of endospores.

In embodiments, is provided a method for processing dry powder for protein analysis. In certain embodiments is provided a method for detecting the presence of dry bacterial spores using a protein detection reagent and solid particles. These methods comprise: a) collecting the dry powder suspected of comprising dry bacterial spores; b) contacting solid particles with the collected dry bacterial spores; c) applying a mechanical force sufficient to break open the spores to increase available protein; and, d) exposing the dry bacterial spores, either before breaking open or after, to at least one reagent that produces color in the presence of protein, wherein a color change indicates the presence of protein and the suspected dry bacterial spores in the sample.

In embodiments, bacterial endospores are found in a dry powder sample. This sample may be any dry substance suspected of containing protein, in particular dry bacterial spores such as endospores. In embodiments, the bacterial spores may be pathogenic and include, but not limited to *Bacillus* or *Clostridium*. In embodiments, the pathogenic spores in the sample suspected of comprising dry bacterial spores are *Bacillus cereus* or *Bacillus anthracis* spores. In embodiments, the sample may comprise spores used as biowarfare agents or those found on food stuff and considered harmful to humans. In embodiments, the biowarfare agents in the sample suspected of comprising dry bacterial spores comprise *Bacillus anthracis* or *Clostridium botulinum*.

Figure 11:
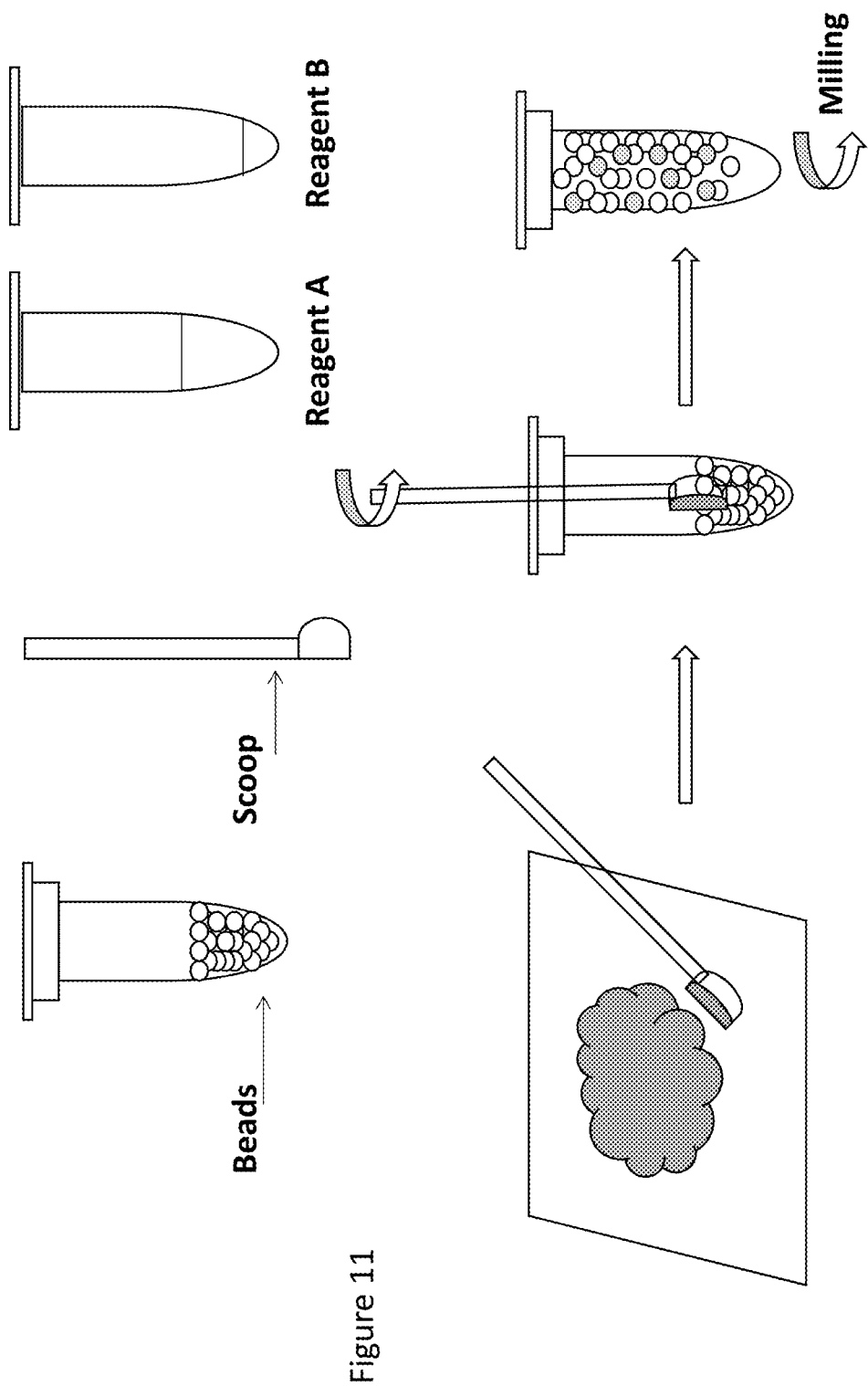
FIGS. 11-17 Show various assay configurations for protein detection from endospores using milling beads and a mechanical force to disrupt the endospores.
Figure 12:
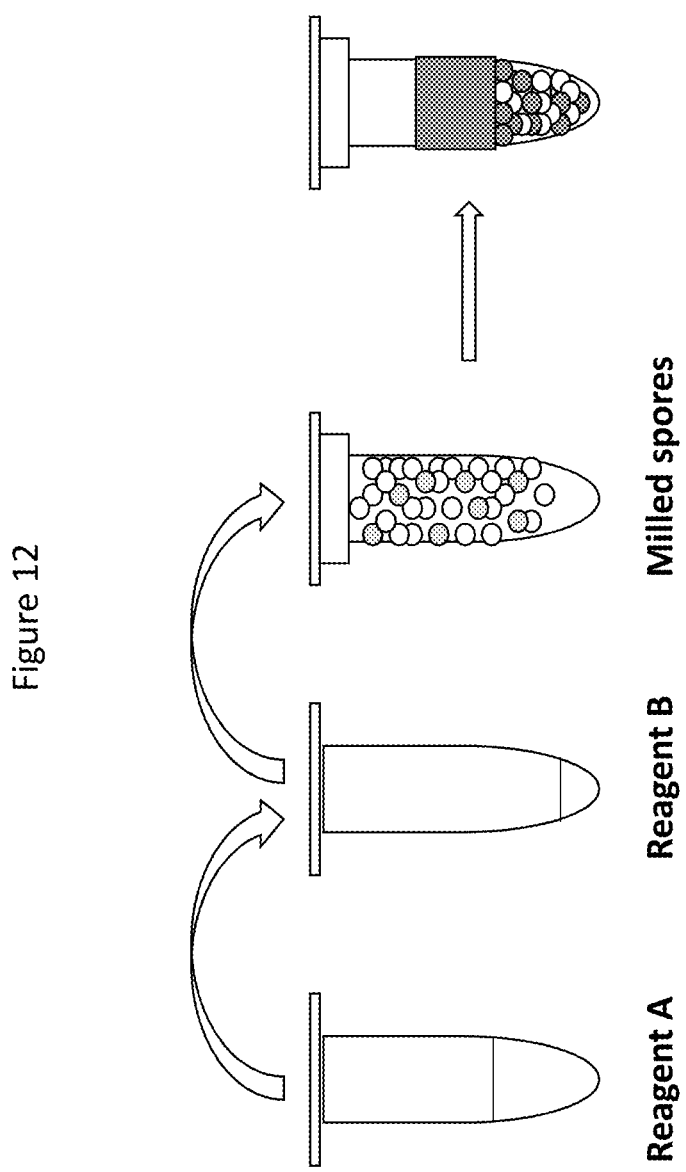
Figure 13:
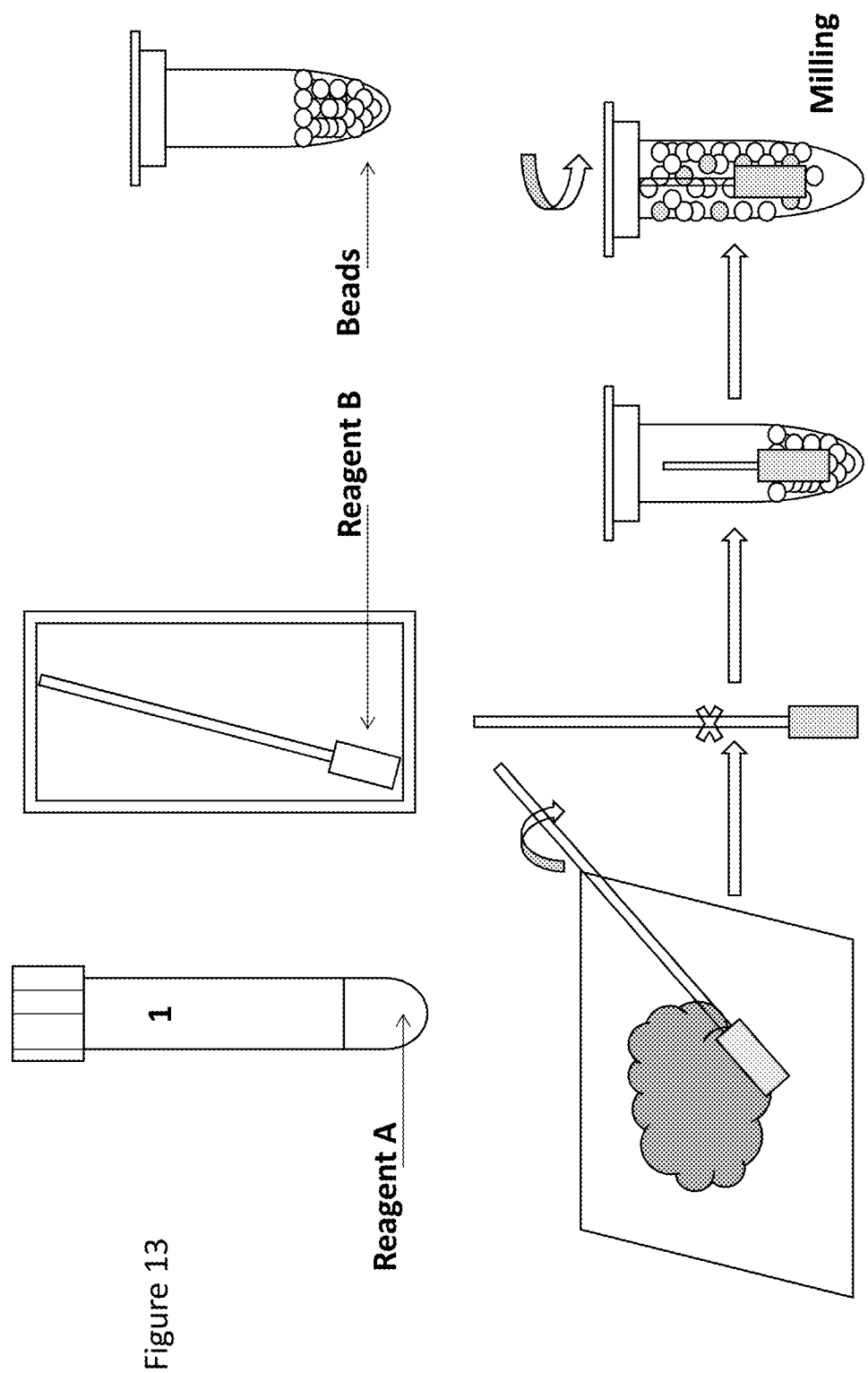
Figure 14:
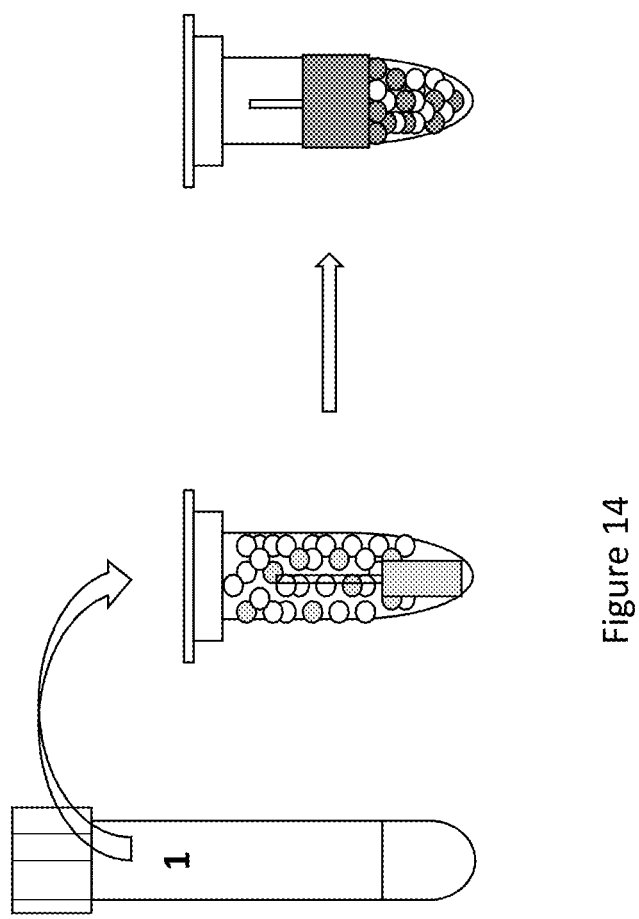
Figure 15:
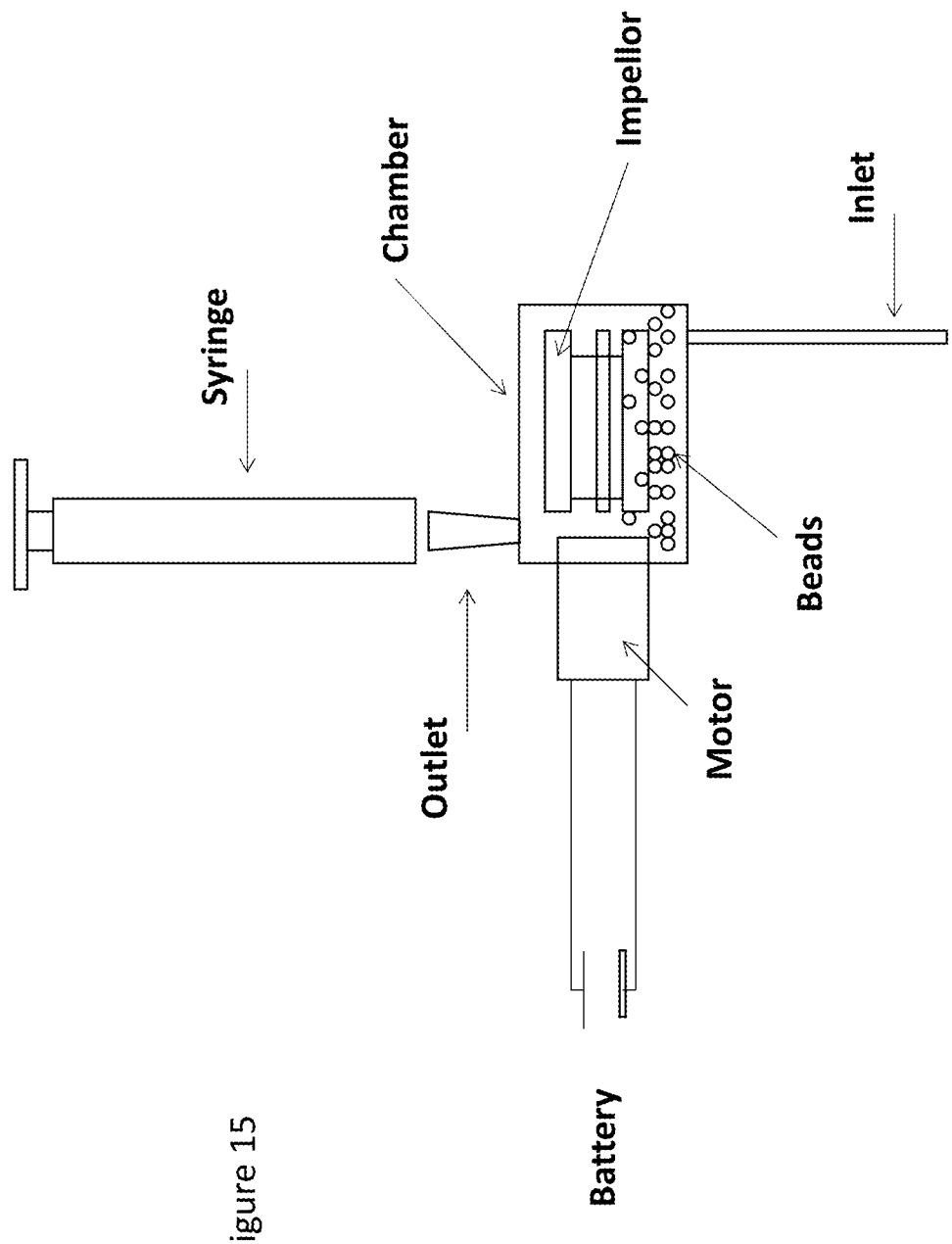
Figure 16:
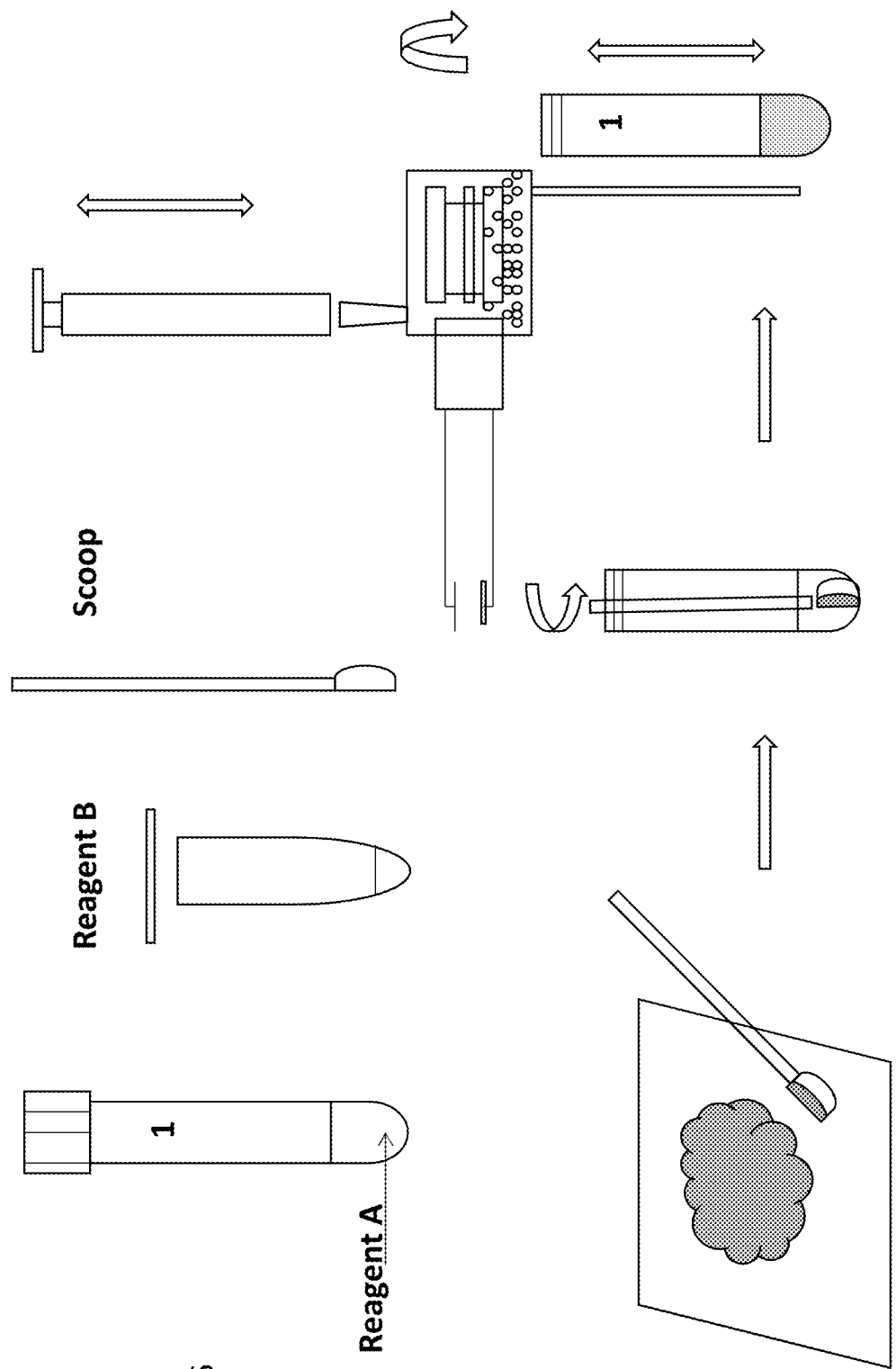
Figure 17:
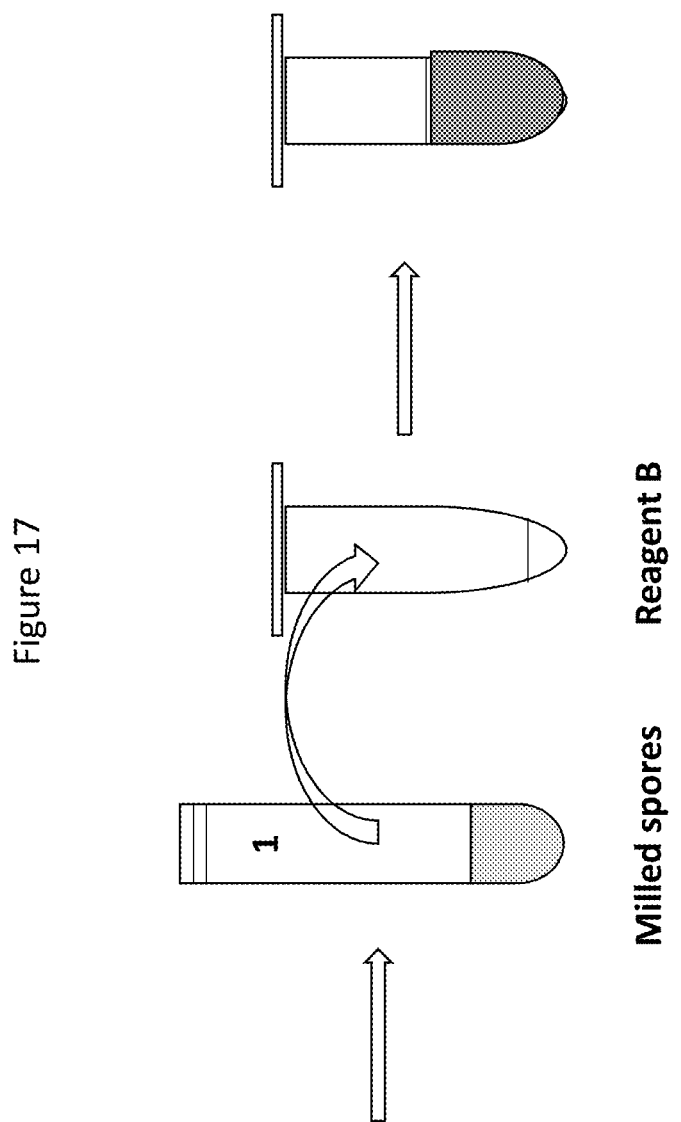
Figure 18:
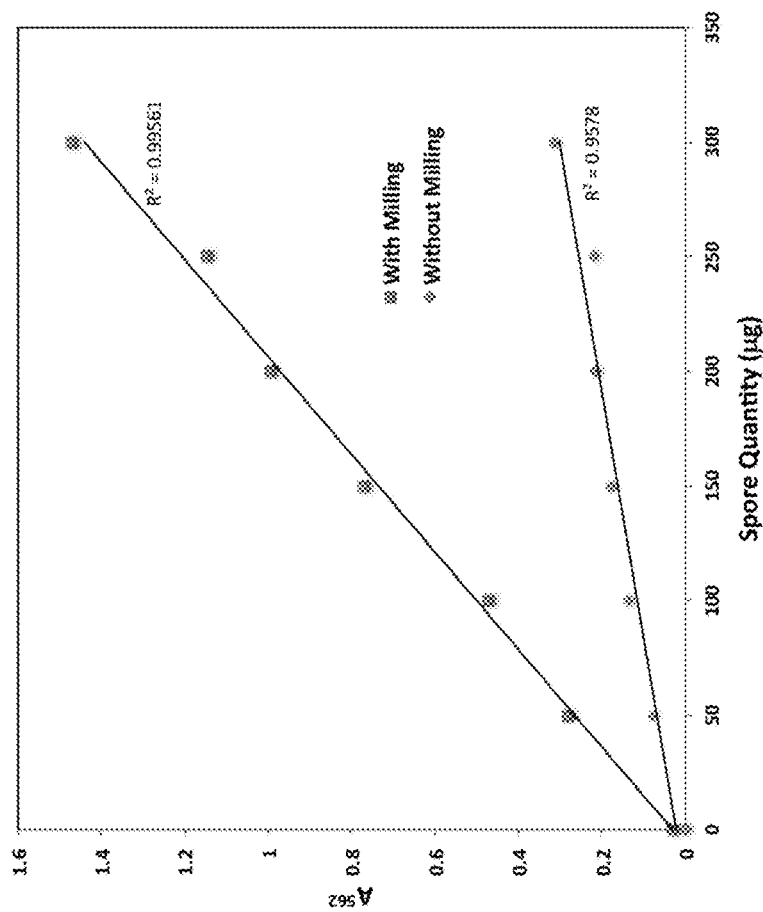
FIG. 18 Shows detection of spore protein over a range of 0-300 µg with and without bead milling using Biocheck® reagents.

The sample suspected of containing protein or bacterial spores is collected by any means useful and known to one of skill in art. In certain embodiments a swab comprised of absorbent material or material configured to capture bacterial spores is used to collect the sample. In one aspect the swab is pre-wetted with an aqueous solution, such as a protein detection reagent or water. In another aspect, the swab is dry when used to collect the sample. In an alternative embodiment, the sample is collected with a small scoop. See FIG. 11. In further embodiments, both a scoop (to collect an initial sample) and a pre-wetter swab is used to collect a second sample to ensure the concentration of spores is high enough for detection.

Once collected the sample is contacted with solid microparticles. These particles can be made from various material, such as glass, metal or zirconia/silica, but with a necessary hardness to break apart an endospore. The particles can range in size, but particularly useful are beads or particles in the range from about 5 µm to about 500 µm. In embodiments, the solid lysing particles are about 50 to about 150 µm in diameter. Milling beads include 100 µm zirconia/silica beads from BioSpec, 100 µm glass beads from BioSpec and 150 µm Garnet mineral sharp particles from MO BIO Laboratories. Any bead or particle may be used with the present methods provided that when used with mechanical force will break open endospores and expose the intrasporal protein (including that found in the coat and cortex) increasing the available intrasporal protein for detection.

In embodiments, the collected sample is placed in a tube (such as a microfuge tube) containing an aliquot of solid microparticles, such as dry milling beads. In embodiments, the milling beads or solid microparticles are 100 µm zirconia/silica beads. In embodiments, the sample suspected of comprising dry bacterial spores is added to the tube with 50 mg, 100 mg, 200 mg or 300 mg of solid microparticles. See FIG. 21. We have found that for a portable field test using microfuge tubes, 300 mg of dry milling beads provides the highest concentration of available protein for testing.

Bacterial endospores have a protein based coating comprising various layers, some of which comprise a protein component. In particular, an exemplary bacterial endospore comprises an outermost layer referred to as an "exosporium" comprising primarily proteins, lipids, and polysaccharides; a second layer below the "exosporium" referred to as a "coat" comprising various spore proteins and comprising primarily insoluble proteins; a third layer below the "coat" referred to as a "cortex" comprising loosely linked peptidoglycans; a fourth layer below the "cortex" referred to as an "inner membrane" comprises primarily lipids; and a "core" comprising nucleic acids and proteins of the spore. The inner membrane protects the spore "core" by providing impenetrable barrier to most compounds. Therefore, in order to access the intrasporal proteins of a spore (including those in the coat and cortex) such that various protein detection techniques can be utilized, the spore must be disrupted or broken apart wherein those proteins are exposed.

Thus, in certain embodiments herein described physical disruption of a bacterial endospore can be performed according to a process in which disruption of the "exosporium" layer, the "coat" layer, the "cortex" layer, and the "inner membrane" layer is performed such that protein in these layers and cores of the bacterial endospore become accessible to agents capable of detecting the protein. Because physical means, not chemical, are used to break apart the endospores there is little to no interference with protein detection reagents used to measure the available intrasporal protein. In embodiments, chemical reagents are not used to break open endospores or expose intrasporal protein.

Mechanical force (e.g. physical disruption) includes vortexing or any other means known to one of skill in the art that mixes the spores and milling beads to physically break open the spores (e.g. hand grinding). In certain embodiments the vortex is powered by battery. In other embodiments the vortex is powered by A/C, such as available in a laboratory setting.

In certain embodiments the spores and milling beads are placed in an appropriately sized and shaped vessel or sample tube and subjected to vortexing. The amount of time will vary depending on the sample, vessel, speed, solid microparticles and instrumentation used for applying the mechanical force, but readily determined by one of skill in the art. See for example FIG. 22. In certain embodiments the contacted sample is subjected to about 30 seconds to about 10 minutes of vortexing. In one embodiment the contacted sample is subjected to about 1 minute to 5 minutes of vortexing wherein a protein lysate (e.g., available intrasporal protein) is obtained. In another embodiment, the contacted sample is subjected to about 3 minutes of vortexing with a battery powered vortex wherein a protein lysate (e.g., available intrasporal protein) is obtained.

In other embodiments, a cell disruptor such as an OmniLyse Disruptor (J. Clinical Microbiology, July 2011 p. 2533-2539) is used with the solid microparticles to provide the mechanical force necessary to disrupt and break open the spores.

In certain embodiments, the spores, following mechanical force treatment with the solid microparticles, are contacted with a non-specific protein detection reagent, wherein a color change or a degree of color change indicates the presence of protein or relative protein concentration. See Example 1. In an alternative embodiment, the spores are contacted with at least one protein detection reagent prior to bead milling of the spores. See Example 3. The protein detection reagent may be pre-wetted on the swab used for sample collection or added to the sample vessel before or after addition of the sample or milling beads, but before lysing the spores.

Figure 9:
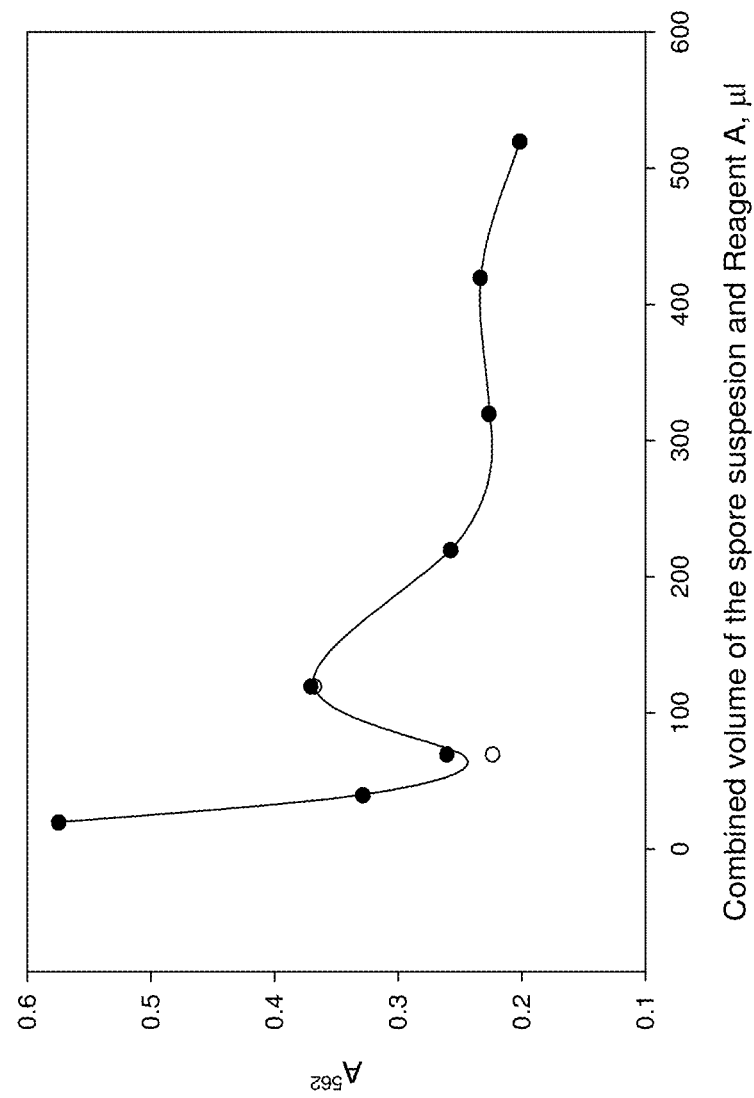
FIG. 9 Shows optimization of the volumes of the spore suspension using 300 mg/tube of milling beads with a 30-second beating.

Surprisingly, milling the beads (e.g. solid microparticles) in the absence of a protein detection reagent or in suspension (dry milling) and then applying the protein detection reagent provided a 25-fold increase in signal as compared to methods that did not break open the spores by mechanical force. See FIG. 9 and Example 4. Accordingly, in certain embodiments, the sample is dry milled with the milling beads (e.g. applying a mechanical force sufficient to break open the spores to increase available protein) wherein the sample is transferred to a testing device containing a protein detection reagent (e.g. at least one reagent that produces color in the presence of protein). In certain embodiments, the dry milled sample is transferred to another tube with the aid of a pre-wetted swab, such as with BCA reagent B (e.g. BIO-CHECK Reagent B; 20/20 GeneSystems, Inc. of Rockville, Md., the BIOCHECK kit is more fully described in U.S. Pat. Nos. 6,770,485 and 6,958,242, the subject matter of which is incorporated herein by reference, in their entireties).

In certain other aspects the dry milled sample is poured into another tube, wherein the tube contains Reagent A and Reagent B is added. In one aspect, reagent B is added as a pre-wetted swab. See Example 7. Reagent A is a bicinchoninic acid solution, which may comprise sodium carbonate, sodium bicarbonate or other buffering components in addition to bicinchoninic acid and Reagent B is a copper sulfate solution. Smith, P. K., et al. (1985) Measurement of Protein using Bicinchoninic Acid. *Anal Biochem* 150:76-85.

The instant methods use colorimetric protein detection reagents for the detection of the bacterial protein, however any protein detection reagent can be utilized with the present methods that increase the amount of available protein for detection. Additional instrumentation may be needed depending on the protein detection reagent used. Most colorimetric protein assay methods can be divided into two groups: those involving protein-copper chelation with secondary detection of the reduced copper and those based on protein-dye binding with direct detection of the color change associated with the bound dye. Bicinchoninic acid (BCA), (modified) Lowry protein assays (Folin-Ciocalteu reagent; a mixture of phosphotungstic acid and phosphomolybdic acid) and the biuret test are examples of protein assays based on copper chelation, wherein $Cu^{2+}$-protein complexes are formed under alkaline conditions, followed by reduction to $Cu^+$, for example by aromatic residues of the protein or peptide bonds (the biuret reaction), wherein the amount of reduction is proportional to the protein present. In the BCA protein assay, the colorimetric detection reagent forms a color complex with the $Cu^+$ providing a proxy for the protein present in a sample. For the Lowry protein assay, $Cu^+$ is oxidized back to $Cu^{2+}$ by the molybdic acid in the Folin-Ciocalteu reagent, which forms molybdenum blue.

The Bradford protein assay, which uses Coomassie blue reagent and is also referred to as a Coomassie assay, is based on protein-dye binding. That protein assay is dependent on the amino acid composition of the measured protein. Under acidic conditions the red form of the dye is converted to blue. In embodiments, at least one reagent that produces color in the presence of protein are those reagents used in the BCA protein assay, Lowry protein assay, Bradford protein assay, biuret protein assay or Coomassie assay. In embodiments, the protein detection reagent comprises bicinchoninic acid (BCA), a mixture of phosphotungstic acid and phosphomolybdic acid, or Coomassie blue dye.

In embodiments, the protein in the protein lysate is detected using bicinchoninic acid, also known as a BCA protein assay. The macromolecular structure of protein, the number of peptide bonds and the presence of four particular amino acids (cysteine, cystine, tryptophan and tyrosine) are reported to be responsible for color formation with BCA. Wiechelman, K., et al. (1988). Investigation of the bicinchoninic acid protein assay: Identification of the groups responsible for color formation. *Anal Biochem* 175:231-7. Accordingly, in embodiments the protein concentrations may be determined with reference to a known concentration of a common protein such as bovine serum albumin (BSA). In embodiments, a series of dilutions of known concentration are prepared from the reference protein such as BSA and assayed alongside the sample suspected of comprising dry bacterial spores wherein the concentration of each sample may be determined based on a standard curve. For the BCA protein assay, total protein concentration is exhibited by a color change of the sample solution from green to purple in proportion to protein concentration, which can then be measured using colorimetric techniques such as measuring absorbance. Any assay known to one of skill in the art that measures the presence and/or concentration of protein in a sample may be used in the present methods, including non-specific protein assays (e.g. BCA protein assay) or specific protein assays utilizing, for example, labeled antibodies in an immuno assay format.

Using appropriate controls (e.g. reference protein disclosed above), the measured protein can be quantified. The methods disclosed herein provide at least a 5× increase in sensitivity as compared to a method using similar protein detection reagents but without the step of mechanically exposing the intrasporal protein (including protein in the coat and cortex).

In other embodiments, the presence or absence of the intrasporal protein is determined by evaluating visual color change (e.g. colorless to purple).

Kits

In embodiments provided herein are kits for detecting the presence of dry bacterial spores in a sample, such as dry powder, suspected of comprising dry bacterial spores, using a protein detection reagent and solid microparticles. The kits may be configured for use in a laboratory setting or a portable filed based (non-laboratory) setting.

In one embodiment, a kit comprises at least one aliquot of solid microparticles (e g milling beads); a sample collection device such as mini scoop or a swab; at least one sample tube for bead milling (e.g. a tube used for applying a mechanical force sufficient to break open the spores to increase available protein) such as a microfuge tube and a protein detection reagent (e.g. at least one reagent that produces color in the presence of protein). The kit may further comprise a device for applying mechanical force to the milling beads such as a vortex; additional tubes and/or instructions. In one aspect the vortex is batter powered. In another aspect, the protein detection reagent comprises BCA Reagent A (a bicinchoninic acid solution) and Reagent B (copper sulfate solution).

In certain embodiments, a kit comprises an aliquot of solid microparticles in a microfuge tube; a mini scoop for sample collection; a pre-wetted swab with BCA Reagent B (copper sulfate solution) and a tube comprising Reagent A (a bicinchoninic acid solution). The kit may further comprise a battery powered vortex and/or instructions. In an alternative embodiment, the BCA Reagent B (copper sulfate solution) is provided in a separate container, such as a dropper for addition to the tube containing Reagent A (bicinchoninic acid solution) after sample addition.

EXAMPLES

The Examples below are given so as to illustrate the practice of the disclosed methods. They are not intended to limit or define the entire scope of this disclosure.

Comparative Example 1—Sensitivity and Limit of Detection of BSA and an Endospore Suspension With a Non-Specific Colorimetric Protein Detection Reagent Materials:

The lyophilized powder of *Bacillus cereus* T endospores was prepared at University of Maryland (College Park, Md.) and received from Prof. J. N. Hansen (Vary, J. C., and H. O. Halvorson. 1965. Kinetics of germination of *Bacillus* spores. J. Bacteriol. 89:1340-1347). The bovine serum albumin, BSA, code 001-000-162 was purchased from Jackson ImmunoResearch Laboratories. The compositions of Reagents A (a bicinchoninic acid solution) and B (copper sulfate solution) of the BCA protein assay are disclosed above and by Smith, P. K., et al. (1985) Measurement of protein using bicinchoninic acid. Analyt. Biochem. 150:76-85. The assay was performed at a temperature controlled by a Cole-Parmer Polystat® cooling/heating circulating bath, model 12108-10. The bench-top refrigerated centrifuge was Heraeus' Biofuge Fresco with the rotor #3329. The absorbance readings at 562 nm were done using Perkin Elmer's Lambda 2S spectrophotometer and Brand's UV-cuvettes micro (#7592 30) with the 10-mm path length.

Method:

Samples containing up to 100 µg BSA or 7.5 mg *B. cereus* endospores in 20 µl of PBS were admixed with 500 µl of BCA Reagent A and the protein detection reaction with the available protein was initiated by adding 40 µl of BCA Reagent B. After the 5-min incubation at a selected temperature the mixtures were centrifuged at 5° C. and 13000 rpm for 1 min and then the supernatants were immediately transferred into cuvettes where absorbance was measured at 562 nm.

Results:

The assessment of sensitivity of the basic protein assay towards a fully soluble protein and an endospore suspension is based on dependences of $A^{562}$ vs. amount of an analyte per probe and an assumption that the dye could distinguish the purple color increase equal to 0.1 $A^{562}$ over a control. Based on that, it was concluded the limit of detection (LOD) of BSA at 70° F. was 8.5 µg while that of *B. cereus* endospores was about 25 times higher, 212 µg. See FIG. 1. At 100° F. the LOD for *B. cereus* endospores decreases to 120 µg and increases to 476 µg at 40° F. (data not shown).

Using the curve obtained with BSA in FIG. 1 as a calibration, 1 mg of the spores corresponds to about 33 µg of a detectable protein. Such an amount, 3% of the sample mass, represents only a small fraction of the endospore proteins.

Additional factors affecting the BIOCHECK (BCA protein assay) test sensitivity compared to the basic protein assay.

Light Scattering on Spores:

The method used above includes a short centrifugation step to sediment the spores just before the $A^{562}$ reading. That was used to avoid the light scattering on the spores that could otherwise compromise the absorbance measurement. As a field test the BioCheck® test doesn't require the centrifugation step, meaning that the pink color assessment could be done on turbid (cloudy) probes and thus the test's LODs might be actually higher than ones determined above. One could expect that the light scattering on fully disrupted spores will be less significant or even negligible.

Swab Effects

The BioCheck® kit contains a pouch with the sealed knitted polyester swab 758B (ITW Texwipe) wetted with about 40 µl of BCA Reagent B. The testing starts when loading the swab with a dry powder and then inserting the swab into a test tube with 500 µl of BCA Reagent A; no agitation or vortexing is required by the test protocol.

FIG. 2 shows that just the presence of the swab causes about 10% inhibition of the color development no matter what is in the test mixtures, BSA or endospores. The effect of a 10 second vortexing step upon inserting the swab wetted with BCA Reagent B is evaluated in FIG. 3; BSA detection initiated without (bars 1 and 3) or with (bars 2, 4 and 5) a 10 second vortexing step wherein Reagent B (copper sulfate solution) was delivered by a swab in a volume of 10 µl (bars 1 and 2) or 40 µl (Bars 3 and 4), no swab was used for a control in bar 5. As seen, the mixing alone might increase the test sensitivity in regard of soluble proteins up to three times.

The swab effect was further analyzed using Reagent A and B of the Biocheck® kit, see Example 6 below.

Example 1—Comparison of Different Milling Beads and Particles Using a Sequential Milling and Protein Detection Process Material:

(in addition to ones described in Comparative Example 1) The disruption of *B. cereus* T spores was performed in regular 500-μl microtest vials with BioSpec Products' 100-μm beads made of zirconia/silica (#11079101z, 380 mg per tube) or glass (#11079101, 260 mg per tube). Also, the Garnet mineral sharp particles with an average size of 150 µm (MO BIO Laboratories, #12224, 260 mg per tube) were tested. The disruptor was a Vortex-Genie® 2 Vortex mixer (Scientific Industries) supplemented by MO BIO Vortex adapter 13000-V1. To hold there the 500-µl tubes firmly, the adapter's plastic clips were provided with insertions cut from a Tubclair AL hose (#147440).

Methods:

250 µg of the spores in 20 µl was placed on the top of the milling beads or particles in the 500-µl vial. After inserting the vial into the clip with the vial cap facing the center of the adapter, the 5-min milling was performed at the maximum speed of the Vortex mixer. After the milling, the vial's content was mixed with 500 µl of Reagent A, 40 µl of Reagent B and then incubated for 5 min at a room temperature. $A^{562}$ was read immediately after the mixture clarification with the 1-min centrifugation (as in Comparative Method 1).

Results:

Data in FIG. 4 show that the spore milling with zirconia/silica beads provides more than a 5-fold increase in the spore protein available for detection by the basic assay (compare bars 1 (without spore milling) and 4 (with milling)). The glass beads were slightly less effective (compare bars 3 (glass) and 4 (zirconia/silica)) that zirconia/silica beads, while the use of the irregularly shaped Garnet particles (bar 2) resulted only in the modest—just under 2-fold—increase in the assay sensitivity (bars 2 and 1).

Unless specified, 100-µm zirconia/silica milling beads were used in the following examples.

Example 2A—Sequential Bead Milling and Protein Detection of Endospores

Material and Methods:

This example was performed using the materials and methods of described in Example 1, except that only zirconia/silica milling beads were used to disrupt the endospores.

Results:

Data in FIG. 5 demonstrate (i) that the zirconia/silica beads are effective not only at the above selected spore amount (i.e. 250 µg) but over the spore entire range of 0-300 µg and (ii) that with their use in the spore milling the LOD drops down to 28-29 µg at a room temperature.

Example 2B—Validation of Sequential Bead Milling and Protein Detection of Endospores Using Zirconia/Silica Beads With BioCheck® Reagents Material and Methods:

Aliquots of 0, 50, 100, 150, 250 and 300 µg of spores in 20 µL of water each were added on top of 380 mg BioSpec 100 µm zirconia/silica (Cat #11079101z) in 1.5-mL microfuge tubes. Tubes were vortexed for 5 minutes at maximum rate on the MO BIO Lab Vortex-Genie 2 with the multi-tube adapter. Control test cases of the same spore aliquots were performed without beads or milling. After milling, 500 µL of Biocheck® Reagent A and 40 µL of Biocheck® Reagent B (Reagent A and Reagent B correspond to Reagent A and B of the BCA assay) was added to each tube, gently mixed by capping and tilting the tubes twice, and incubated for 5 min. All reactions were clarified by centrifugation for 1 min at 16,100×g, supernatants transferred to disposable UV cuvettes, and read for $A^{562}$ in a UV/Vis spectrophotometer (Ultrospec 2000, Pharmacia Biotech).

Results:

Titration curves of positive (with vortexing/milling) and negative (without vortexing/milling) are shown in FIG. 18. Linear regression curves were overlaid yielding high R-squared values (>0.95 for both cases). The range of signal improvement of positive over negative samples was 123-140% with an average improvement of 131%±6.38% (one standard deviation).

The validation data demonstrated a more linear relationship between spore quantity and $A^{562}$ as compared with that provided in FIG. 5. An additional difference is the greater dynamic signal range seen in the validation data as compared with FIG. 5. However, the signal improvement seem in FIG. 5 and FIG. 18 are in agreement, wherein FIG. 5 demonstrates a range of signal improvement of positive over negative samples of 126-136% with an average improvement of 132%±3.36%, and as described above, the signal improvement of positive over negative samples was 123-140% for the data in FIG. 18 with an average improvement of 131%±6.38%. Example 2A and 2B demonstrate the value of milling spores over a wide concentration range for increasing the available intrasporal protein for detection.

In addition to the quantitative differences in $A^{562}$ signal observed in samples prepared with and without milling, the visual differences are easily distinguishable across the range of tested spore quantities (data not shown).

Example 3—Measurement of Protein Following Bead Milling Disruption of Endospores in the Presence of the Protein Detection Reagents Materials:

The materials were the same as in the above Examples.

Methods: 250 µg of the spores in 20 µl and 500 µl of Reagent A were added to the vials contained 260 mg of the Garnet particles or the glass beads or 380 mg of the zirconia/silica beads and gently mixed. The 5-min milling (performed as in Examples 1) was started immediately after admixing 40 µl of Reagent B. Upon the milling, $A^{562}$ was read immediately after the mixtures clarification with the 1-min centrifugation (as in Comparative Example 1).

Results:

This method design allows for combination of the spore disruption with the protein detection into the single step. However, the milling is usually accompanied by a sample noticeable warming up which should accelerate reactions of Reagents A and B. As seen in FIG. 6 such a factor did not result in $A^{562}$ values higher than those found after the sequential milling and testing.

Example 4—Dry Bead Milling of Endospores For Protein Detection

Dry spores were placed with the help of a scoop into pre-weighed 500-µl vials with 380 mg of zirconia-silica beads. Upon the 90-s beating with Vortex-Genie 2, mixtures of spores and beads were treated with 500 µl of Reagent A and 40 µl of (Reagent B)/4 for 5 min at a room temperature, and centrifuged for 1 min (at 10,000 rpm and 5° C.) before reading $A^{562}$ in the supernatants.

TABLE 1

| Vials with beads, mg | Vials with beads and spores, mg | Spores, µg | $A^{562}$ | $A^{562}$-contr. |
|---|---|---|---|---|
| | | 0 | 0.054 | 0 |
| 639.6 | 640.2 | 600 | 0.851 | 0.797 |
| 629.3 | 629.4 | 100 | 0.884 | 0.830 |
| 635.4 | 635.5 | 100 | 0.886 | 0.832 |
| 633.1 | 633.6 | 500 | 0.914 | 0.860 |

The dry bead milling appeared to produce so much protein that even 100 µg of spores provide $A^{562}$ values close to the upper limit. Dry bead milling appears to provide better availability of protein for the BCA protein assay than the endospore suspension of FIG. 9.

Example 5—Bead Milling and Protein Detection of Endospores and a Cornstarch Control Material and Methods:

Aliquots of 250 µg of either cornstarch or spores in 20 µL water each were added on top of 300 mg BioSpec 100 µm zirconia/silica (Cat #11079101z) in 1.5-mL microfuge tubes. Tubes were vortexed for 30 seconds at maximum rate on the MO BIO Lab Vortex-Genie 2 with the multi-tube adapter. Control test cases of the same cornstarch or spore aliquots were performed without vortexing/milling. After milling, 500 µL of Reagent A and 40 µL of Reagent B was added to each tube, gently mixed by capping and tilting the tubes twice, and incubated for 5 min. All reactions were clarified by centrifugation for 1 min at 16,100×g, supernatants transferred to disposable UV cuvettes, and read for $A^{562}$ in a UV/Vis spectrophotometer (Ultrospec 2000, Pharmacia Biotech).

The experiment was performed twice with two different cornstarch samples. See FIG. 10 and FIG. 19.

Figure 10:
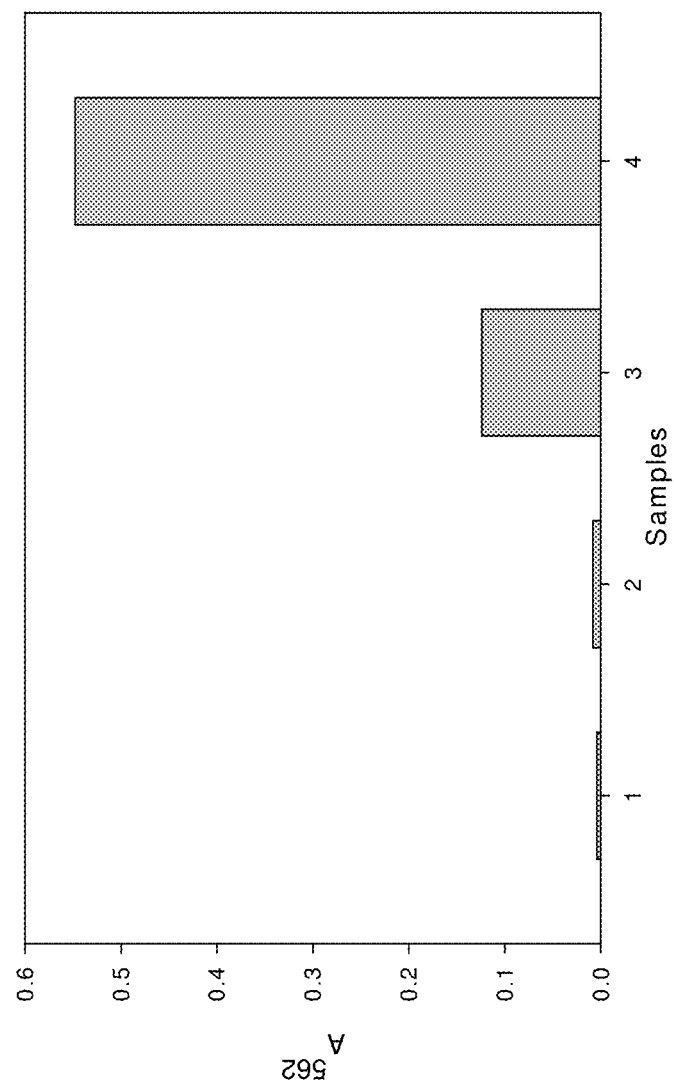
FIG. 10 Shows the bead milling non-protein containing powder such as corn starch does not result in exposure of groups active in the BCA protein assay.
Figure 19:
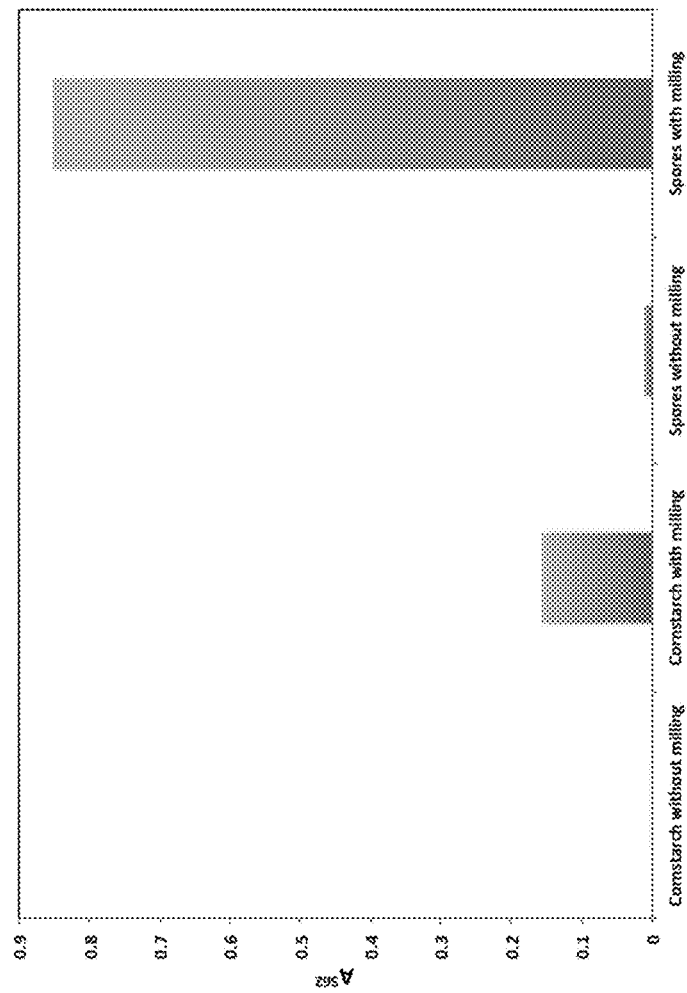
FIG. 19 Shows the comparison of protein detection of cornstarch (negative control) and endospores with and without bead milling using Biocheck® reagents.

Results:

Comparison of protein detection of cornstarch (negative control) and *B. cereus* T spores with and without bead milling is shown in FIGS. 10 and 19. The signal improvement of processing the spores with milling was over 75-fold over the unprocessed (without milling) spore sample and about 4.5-fold over the processed (with milling) negative control cornstarch sample. It was noted that, according to the nutrition facts on the box, the cornstarch used for the data generated in FIG. 19 is 20% protein by weight.

The significant signal improvement of processing the spores with milling over the unprocessed (without milling) spore sample substantiates the data in Example 2 and supports a shorter milling time of 30 seconds.

Example 6—Swab Effect When the Swab is Pre-Wetted With Reagent B

Material and Methods:

Aliquots of 250 µg of Bovine Serum Albumin (BSA, Sigma, Cat # A9647) in 20 µL water each were added to 1.5-mL microfuge tubes. Five hundred (500) µL of Reagent A was added to each tube. Aliquots of either 10 µL or 40 µL of Reagent B were used to wet 758B swabs cut down to fit inside the microfuge tubes and the swabs were added to the tubes. Test cases were vortexed for 10 seconds at maximum rate on the MO BIO Lab Vortex-Genie 2 with the multi-tube adapter. After vortexing, reactions were incubated for 5 min.

Supernatants were transferred to disposable UV cuvettes and read for $A^{562}$ in a UV/Vis spectrophotometer (Ultrospec 2000, Pharmacia Biotech).

Figure 5:
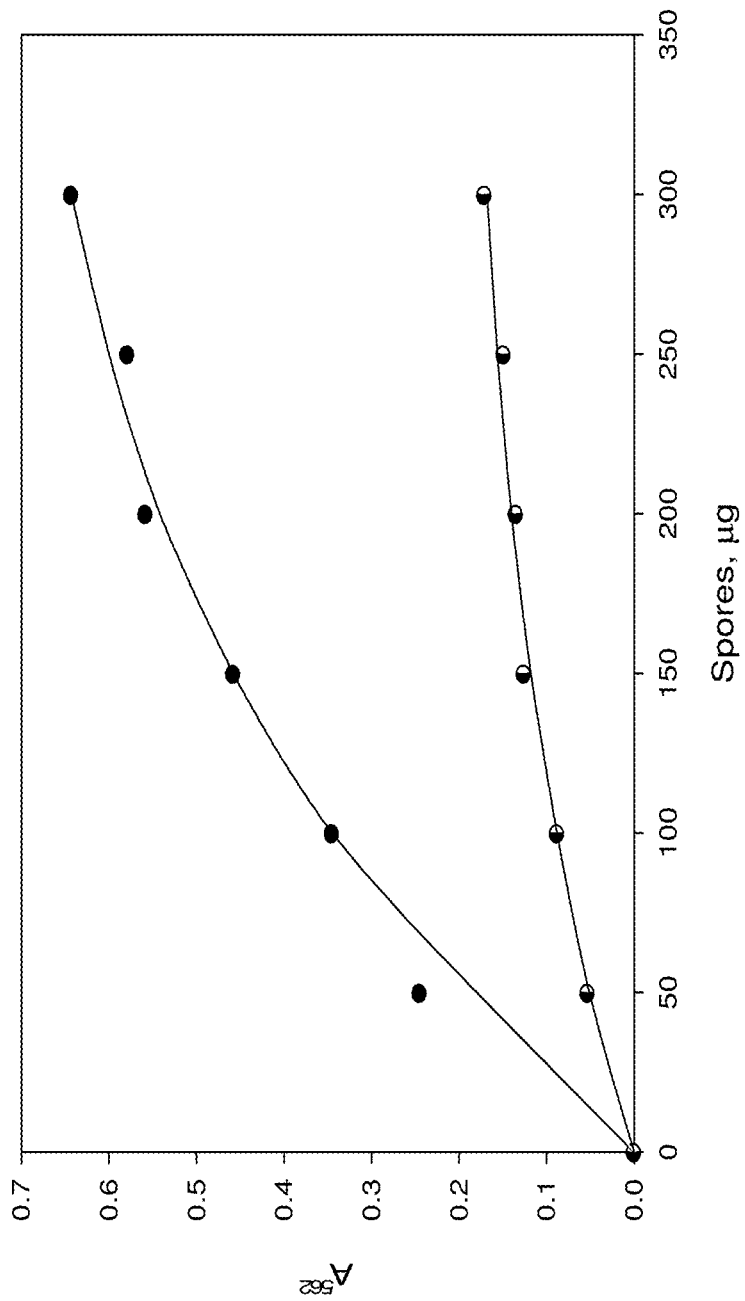
FIG. 5 Shows the detection of endospore protein with and without bead milling using zirconia/silica beads. The endospores were sequentially milled and then protein detection reagent added to the disrupted endospores in the sample.
Figure 6:
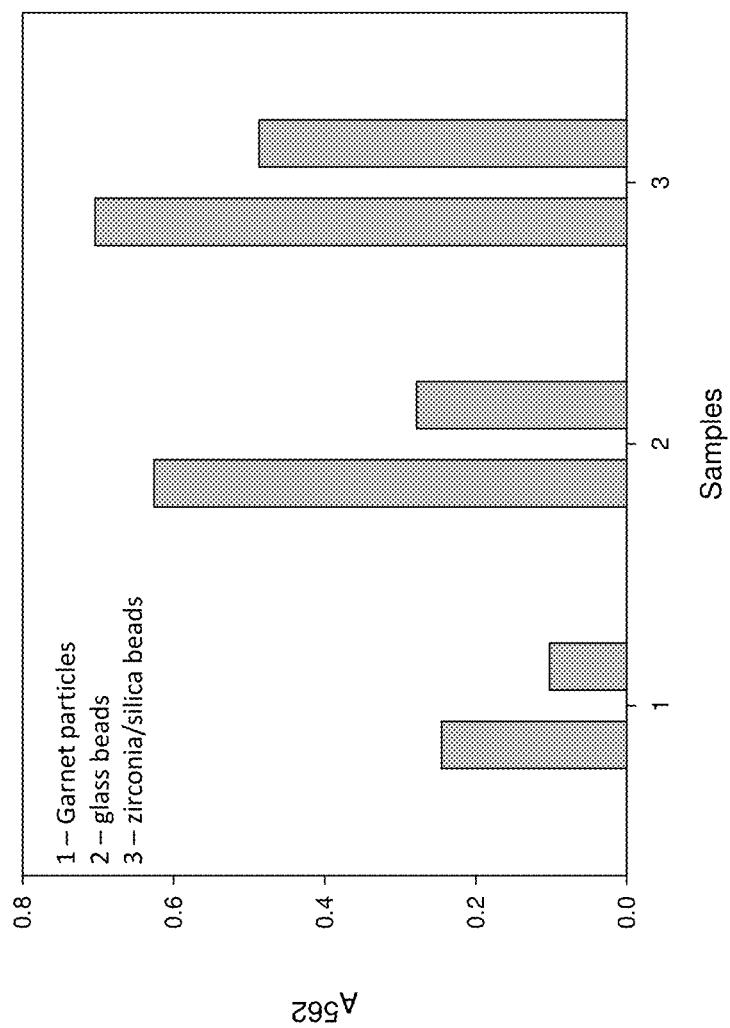
FIG. 6 Shows the detection of endospore protein with bead milling in the presence of the protein detection reagents.
Figure 7:
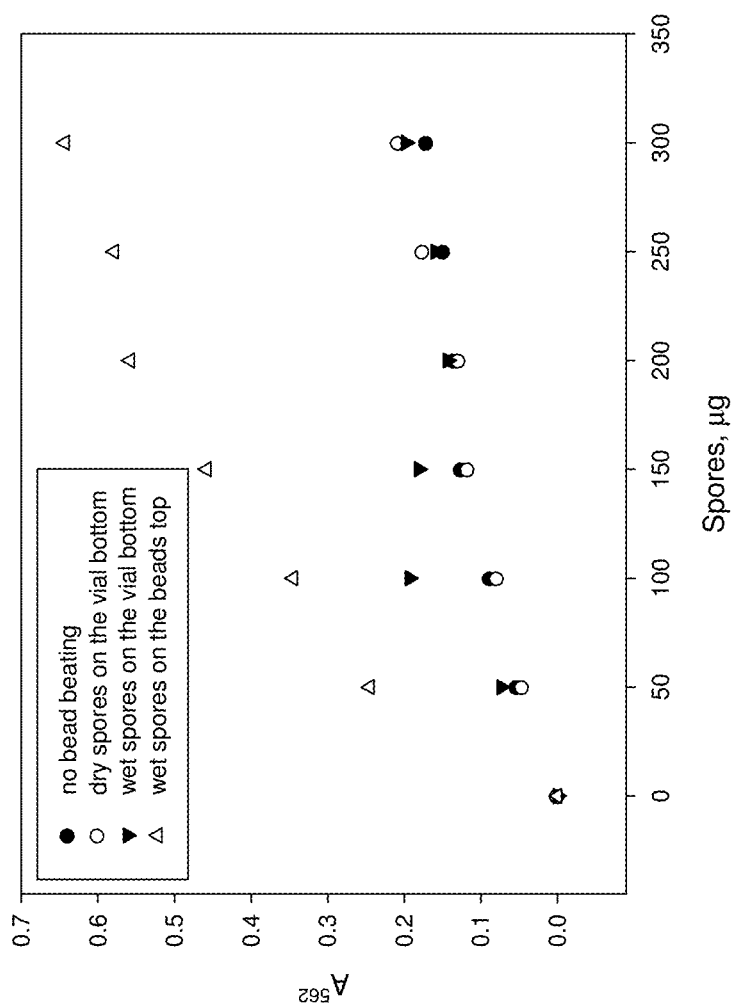
FIG. 7 Shows optimization of placing a spore suspension on top of the milling beads in a tube resulting in about a 5-fold increase in spore protein available for the protein detection reagents.
Figure 8:
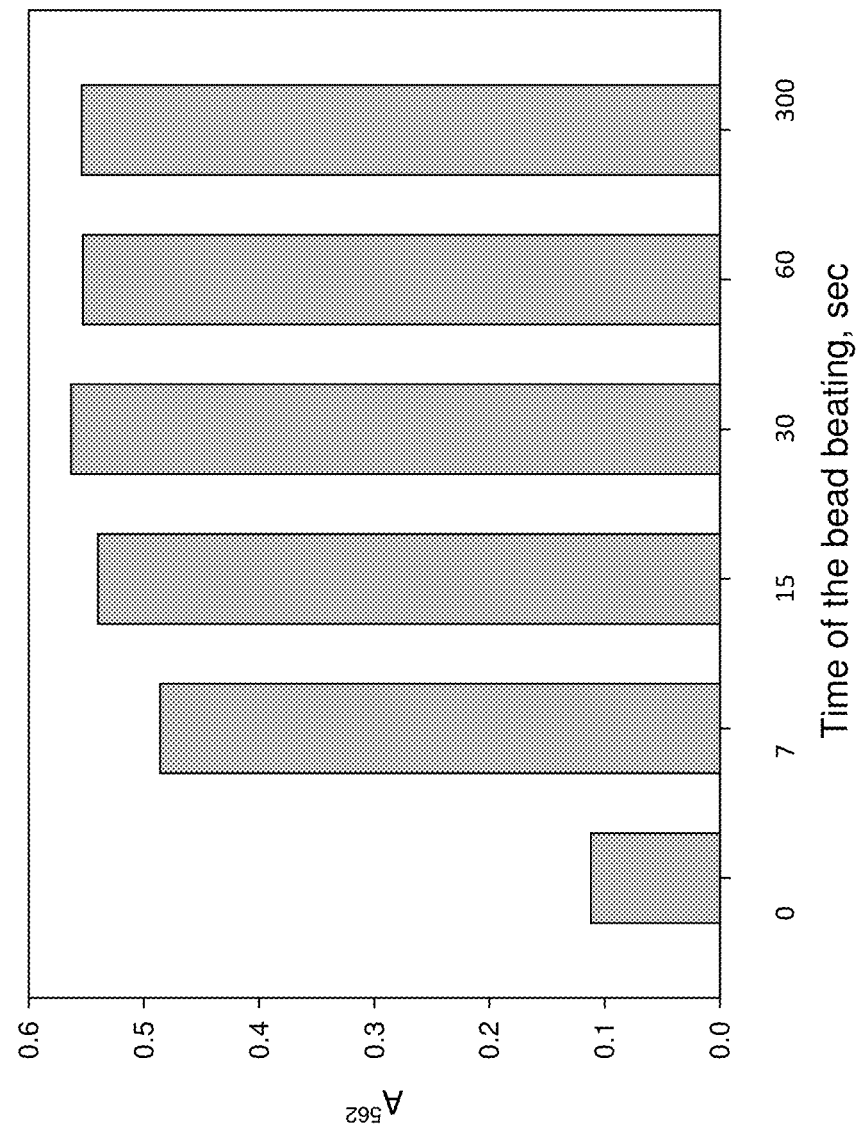
FIG. 8 Shows optimization of time for applying a mechanical force (e.g. vortex) to the milling beads and endospores. The bead beating time was varied from 5 minutes to 7 seconds keeping the bead amount (380 µg) and the spore suspension (20 µl, 250 µg) constant. Results show that 30-second bead beating was sufficient to achieve the maximal color development in the BCA protein assay.

Results:

Results of detection of 250 µg of the model soluble protein BSA initialed without or with 10 seconds of vortexing with Reagent B delivered by 758B swabs are shown in FIG. 5. For reactions utilizing 10 µL of Reagent B, a signal improvement of 334% is observed, and for reactions utilizing 40 µL of Reagent B, a signal improvement of 31% is observed.

Figure 3:
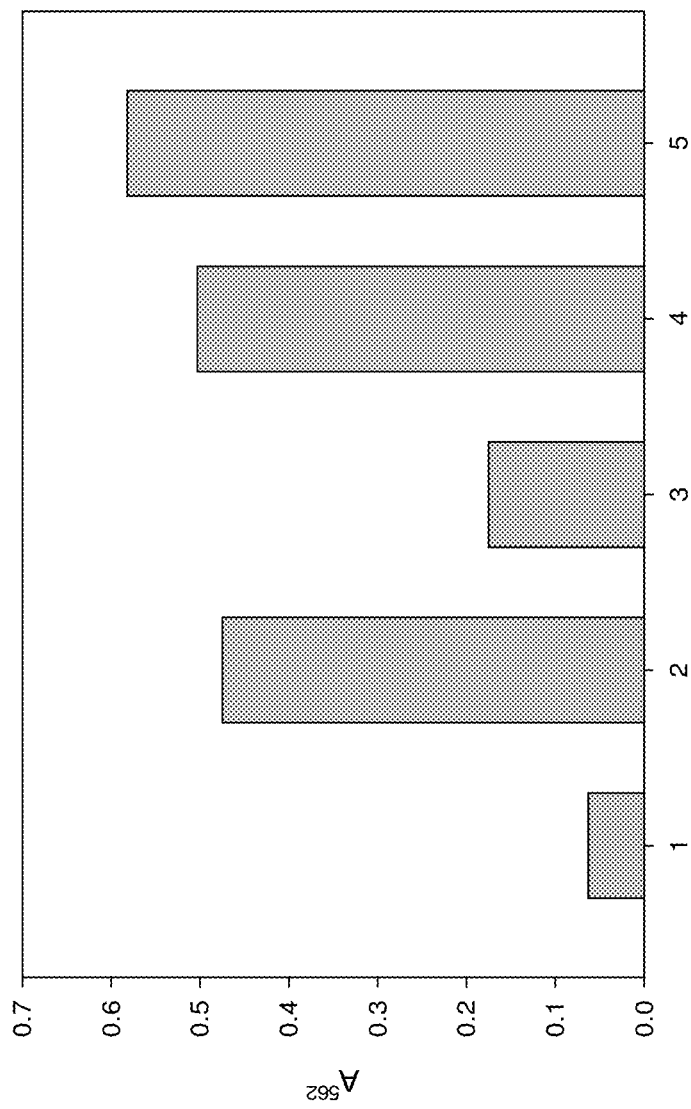
FIG. 3 Shows the effect without (bars 1 and 3) and with (bars 2, 4 and 5) of a short 10 second vortexing step with the swab after wetting with BCA Reagent B and sample collection.
Figure 4:
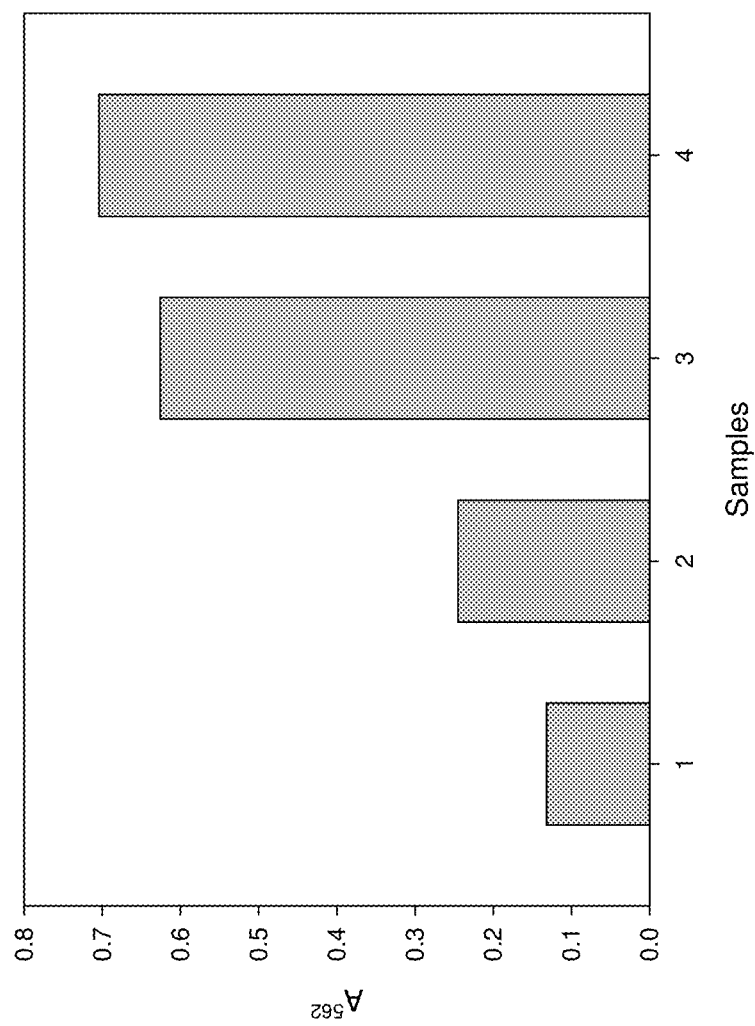
FIG. 4 Shows the comparison of endospore protein detection with different milling beads and particles. The endospores were sequentially milled and then protein detection reagent added to the disrupted endospores in the sample.
Figure 20:
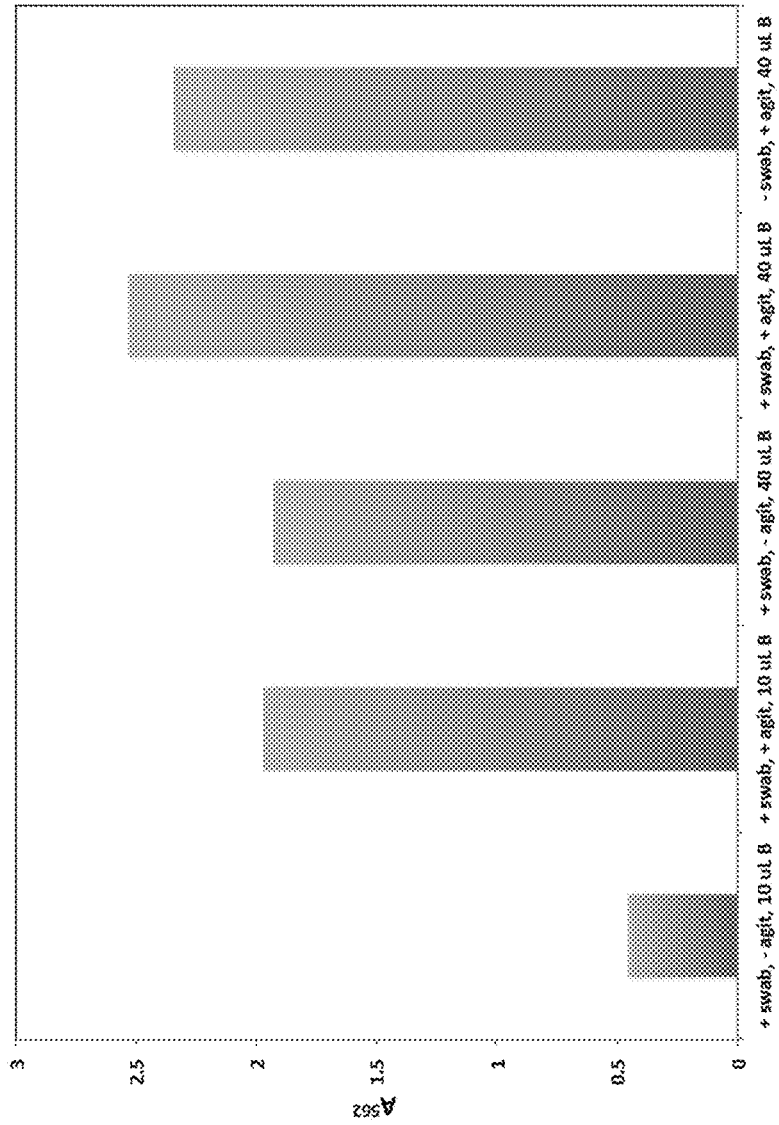
FIG. 20 Shows he effect of vortexing the swab after wetting with Reagent B and sample collection using Biocheck® reagents.

FIG. 3 demonstrates that the use of the 758B swab presently included in the BioCheck® kit causes inhibition of the color development and $A^{562}$ signal. In both FIG. 3 and FIG. 20 when using 10 µL of Reagent B pre-wetted on the swab, significant increases in signal are observed with the addition of 10 s of vortexing. Increases in signal with vortexing were only modest though when 40 µL of Reagent B pre-wetted on the swab (the current volume used in the BioCheck® kit) 31% and 24% in FIG. 20 and FIG. 3, respectively).

These results support the addition of a vortexing or mixing step in the kit protocol when using the 758B swab.

Example 7—Development of a Field Based Test and Kit For Protein Detection of Endospores Using Bead Milling Control Protocol:

The method used as a control for comparison purposes was the protocol per the Biocheck® kit, which included collecting the sample of suspicious powder with a Reagent B (40 µL) pre-wetted swab and then transferring the swab with the sample to Tube 1 of the Biocheck® kit containing Reagent A, and a color change observed when a sufficient amount of protein was present following a brief mixing and a 5 minute incubation period.

Test Design #1:

In certain embodiments, the kit design comprises adding a suspicious powder with a mini scoop to an aliquot of dry milling beads in a microfuge tube, the tube is vortexed (A/C or battery powered), the contents of the tube are transferred to Tube 1 (containing Reagent A) of the Biocheck® kit using a Reagent B pre-wetted swab, and the testing then proceeds as per current kit protocol (e.g. mixing, incubating and evaluating color change).

Test Design #2:

In certain embodiments, the kit design comprises adding a suspicious powder with a mini scoop to an aliquot of dry milling beads in a microfuge tube, the tube is vortexed (A/C or battery powered), the contents of the tube are transferred to Tube 1 of the Biocheck® kit containing Reagent A (e.g. pouring), a Reagent B is added to Tube 1 with a pre-wetted swab, and the testing would proceed as per current kit protocol (e.g. mixing, incubating and evaluating color change).

Various parameters were tested to optimize a portable field based test (without the need for A/C power or to take samples back to a laboratory) for protein detection of endospores. In certain embodiments, an optimized field based test comprises adding a suspicious powder (suspected of containing endospores) with the mini scoop to 300 mg of dry milling beads in a microfuge tube, the tube is vortexed for three minutes using a battery powered vortex, the contents of the tube are transferred to Tube 1 by pouring wherein Tube 1 contains Reagent A of the Biocheck® kit, Reagent B is added to Tube 1 with a pre-wetted swab, and the testing proceeds as per current kit protocol (e.g. mixing, incubating and evaluating color of the liquid sample).

Development of Dry Spore Samples

Example 4 demonstrated the improvement of dry bead milling endospores compared those in a suspension, in addition a suspension of spores in water is not compatible with the current Biocheck® test kit format for use in testing of suspicious powders. Therefore, a dry dilution of spores in a negative background material of comparable consistency (e.g., fineness of powder) was required for further field test development.

First, a reproducible means of aliquoting a dry sample was required that was also compatible with the field test design. Mini scoops (Disposable Anti-Static Polypropylene Powder Scoop, 3-2 mg, Tradewinds Direct, Cole-Parmer Cat #06277-54) were tested for reproducibility by seven (7) repeat measurements of a fine powder (Dextrose, Anhydrous, Powder, J. T. Baker, Cat #1916-01). See FIG. 11. Measurements ranged from 3.3-5.9 mg for a level scoop of powder with an average of 4.5±0.9 mg per scoop.

Next, a selection of negative background material was screened by adding one scoop of material to 50 mg of BioSpec 100 µm zirconia/silica beads (Cat #11079101z) in a 1.5 mL microfuge tube, vortexing with a battery operated vortexer (iBIO Mixer, ITSI, Cat # MQ-020) for 1 min, adding 500 µL of Solution A and 40 µL of Solution B, incubating at room temperature for 5 min, centrifuge clarifying at 16,100×g for 1 min, and reading at $A^{562}$. Spectrophotometer was blanked with a negative reaction (no material sample). Dextrose, cornstarch, and MES monohydrate (2[N-Morpholino]ethanesulfonic acid monohydrate, a common biological buffering agent) gave background signals of 1.194, 0.980, and 0.004, respectively. MES demonstrated a near-zero background signal and was used to create the dry dilutions of spore samples.

Based on the average scoop mass of 4.5 mg, dry dilutions of 1:10, 1:20, and 1:40 of spores to MES were made resulting in single scoop samples of 450, 225, and 112.5 µg of spores. These dry sample quantities were comparable to the wet sample quantities used in Examples 1-3 and 5-6.

Bead Quantity Studies

An assay was performed following the test design #1 wherein a fixed dry spore sample of 225 µg was used in all cases and bead quantities were varied from 50-300 mg.

Figure 21:
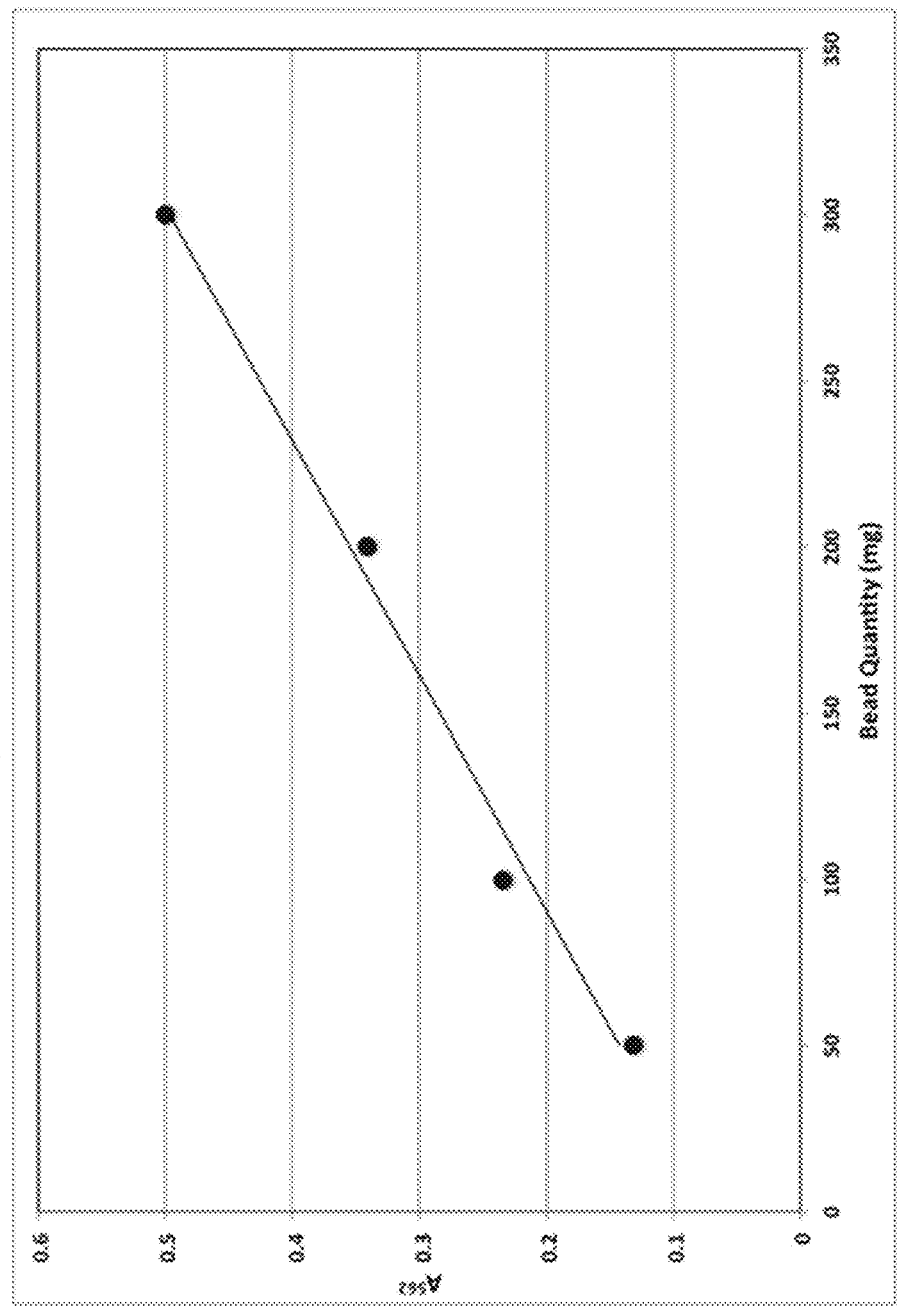
FIG. 21 Shows a linear relationship for detection of protein with different amounts of beads used for milling.

FIG. 21 shows the absorbance signal curves which demonstrates a positive linear relationship to bead quantity. 300 mg of dry beads provides the largest absorbance reading correlating to a higher concentration of available intrasporal protein as compared to bead milling with a smaller amount of beads. In this study, 300 mg of dry beads was the optimum amount to use with a 1.5 µl sample tubes.

Using 300 mg of dry beads is difficult to transfer the sample after bead milling with a pre-wetted swab. Accordingly, design test #2 was used for the remaining testing with 300 mg of dry beads.

Hand Grinding Study

Based on design test #1, a study was done to explore the use of hand grinding of the sample with beads in semi-wet conditions. In this experiment, a microfuge tube was aliquoted with 50 mg of beads. A single mini scoop of 225 µg spore/MES dry sample was added simultaneously with the current kit swab soaked with 40 µL of Reagent B. Sample and beads were ground by hand in microfuge tube for 15 seconds. A swab was used to transfer contents of the tube to a second tube with 500 µL of Reagent A added. The tube was flicked to mix, and reactants were incubated at room temperature for 5 min. The tube was then centrifuged and clarified at 16,100×g for 1 min and read at $A^{562}$. Spectrophotometer was blanked with Solution A alone.

The absorbance of hand ground sample was 0.010 and color was not detectable visually demonstrating that spore samples require vortex milling to result in significant signal increases. While optimal for a field based test, hand grinding did not produce acceptable results.

Battery Powered Vortex Studies

Figure 22:
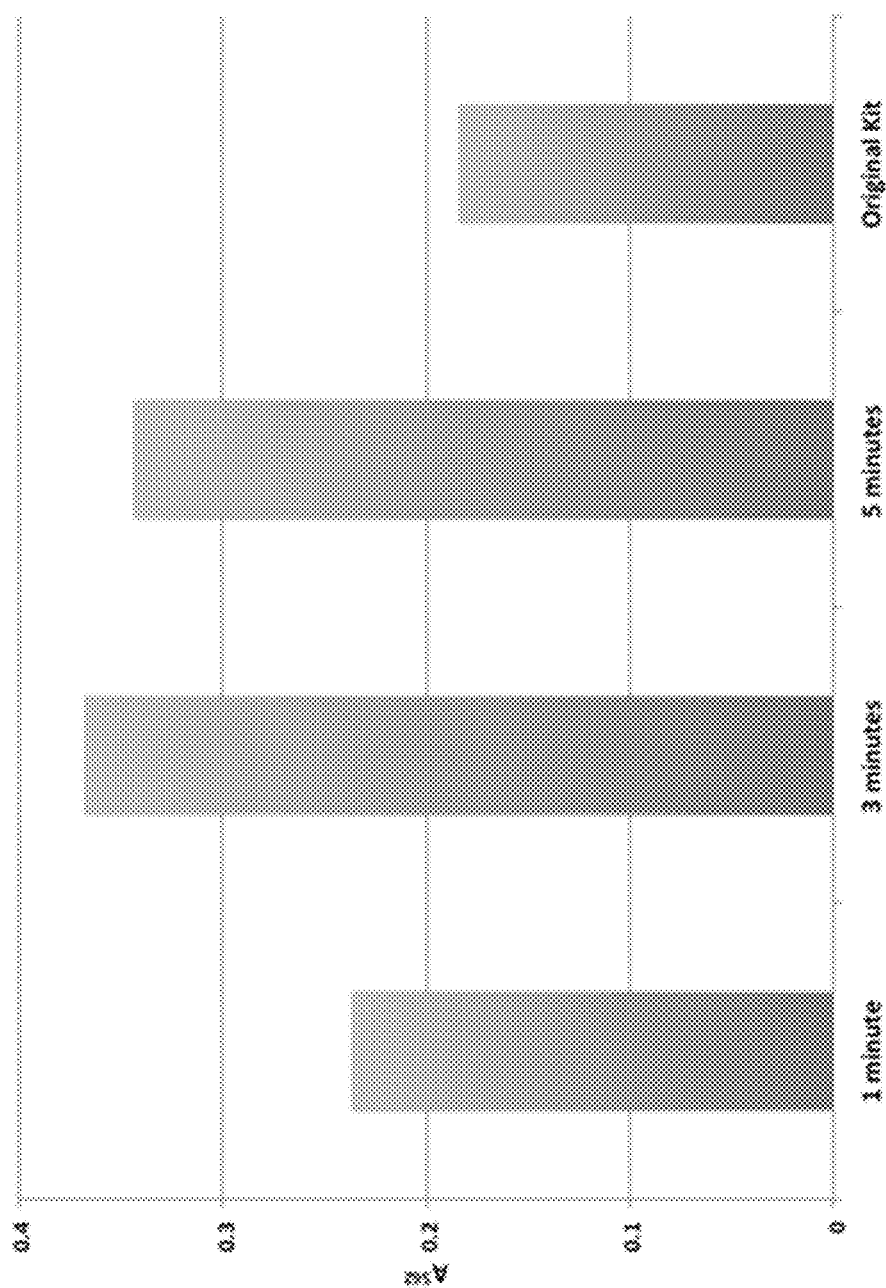
FIG. 22 Shows the difference in detection of protein from endospores with different times using bead milling and a battery operated vortexer.

Based on design test #2, a screen of 1, 3, and 5 minute vortexing was evaluated with a single rounded scoop of the 225 µg spore sample and 300 mg of dry beads. Data is shown in FIG. 22.

Vortexing for 3 minutes resulted in a 100% improvement over the Control protocol and a 55% improvement over the 1 minute vortexing. Color observation (data not shown) also indicated the increased vortexing time results in a significant improvement over the Control protocol.

Testing of Design Test #2 With 300 mg of Beads and 3-Minute Vortexing

Figure 23:
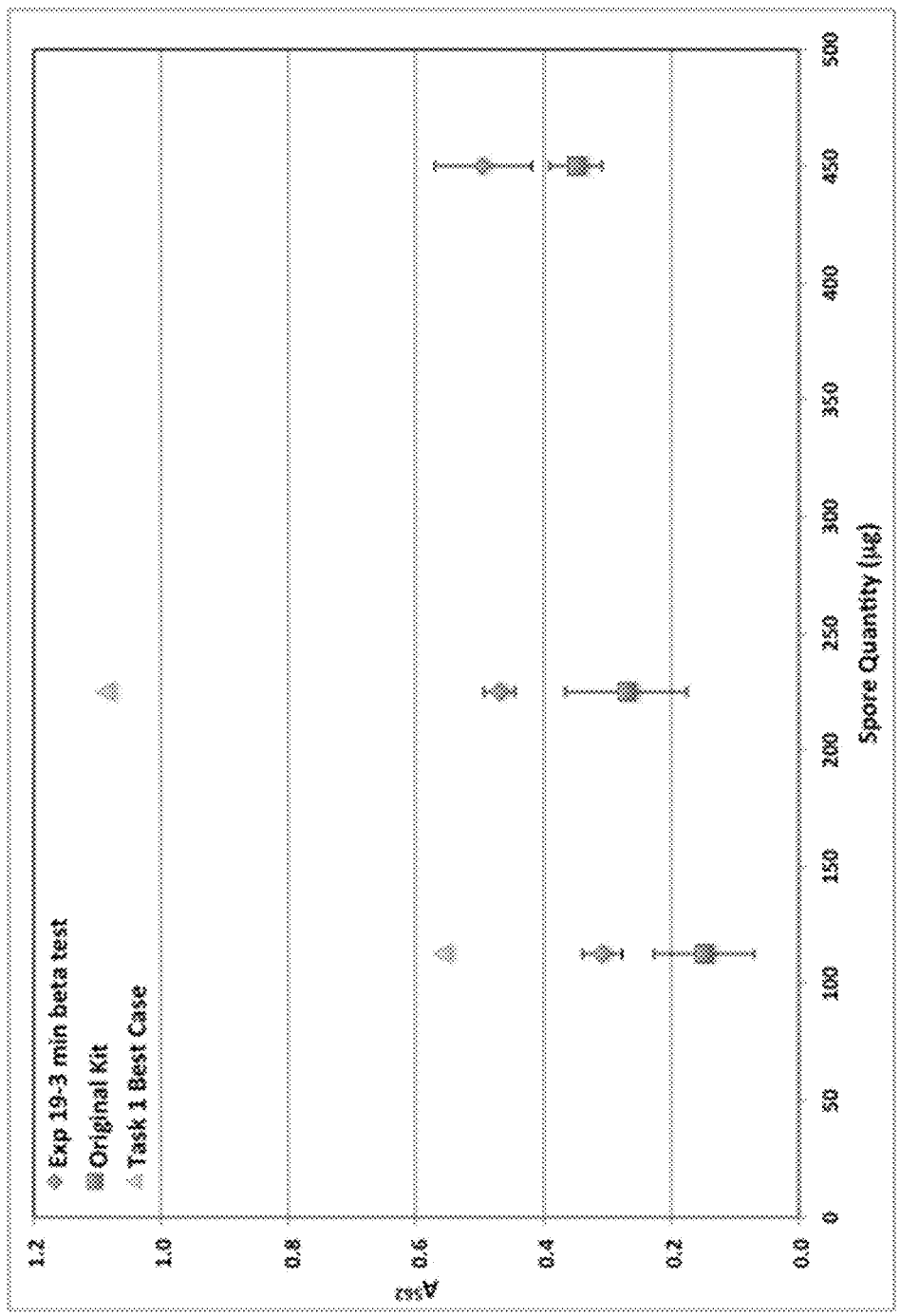
FIG. 23 Shows a comparison of an optimized design test protocol with 300 µg of beads and a 3-minute vortex (battery powered) as compared to a Control protocol (no bead milling) and an A/C powered vortex.

Based on the Vortex Studies, a mix time of 3 minutes was used to evaluate design test #2 using the battery powered vortex at all three test sample concentrations (112.5, 225 and 450 µg spore samples) in triplicate. Data is shown in FIG. 23.

Vortexing for 3 minutes resulted in a 108% improvement over the Control protocol at the lowest tested concentration of 112.5 µg spore sample. Average improvement over the entire range of samples tested was 74% with declining improvement as sample concentration increased. At the low 112.5 µg and mid 225 µg spore sample test cases, the battery vortexing signal was 45% and 57% lower than using a larger multisample A/C vortex with 5 minutes mix time, respectively. Color observation (data not shown) indicated the design test #2 was able to consistently produce a positive protein signal (clear purple color) at the lowest spore sample test case as compared with negative results using the Control protocol.

Using the bead milling process in design test #2 reduced the limit of detection (LOD) to as low as 112.5 µg of purified spores as compared with an LOD of 225 µg using the Control protocol.

Example 8—Limit of Detection Determination With Live Spores

Based on design test #2, a study was performed to determine the limit of detection (LOD) using both live *Bacillus anthracis* Sterne spores (Ames35 strain from BEI Resources) and pure ricin toxin (Vector Labs). The testing was done in triplicate with five concentrations ($10^5$; $10^6$; $10^7$; $10^8$; $10^9$ for *B. anthracis* spores and 975; 1600; 15,625; 62,500; 250,000 ng for ricin toxin) of test samples.

*B. anthracis* spores were grown in Nutrient Broth with CCY salts (Buhr T L, McPherson D C, Gutting B W. 2008. Analysis of broth-cultured *Bacillus atrophaeus* and *Bacillus cereus* spores, J Appl Microbiol 105:1604-1613). Stock concentrations of $10^9$ spores/mL were stored in the fridge (4° C.). On the day of testing, the stock was vortex mixed for 2 minutes immediately prior to making dilutions. Dilutions were made using vendor supplied buffer or Milli Q water if not supplied. Serial dilution samples were vortex mixed in between every dilution to maintain spore suspension.

Ricin was supplied by Vector Labs, L-1090 5 mg/mL (10 mg total) as unconjugated *Ricinus Communis* Agglutinin II. The ricin toxin was stored at 4° C. On the day of testing, dilutions were made using vendor supplied buffer (or Milli Q water if buffer was not supplied) and stored on ice prior to testing (to ensure ricin protein stability).

The limit of detection was $10^7$ for the live spores, a 10-fold increase as compared to testing without the use of milling beads and vortex mixing (data not shown). The limit of detection was 62.5 µg for the ricin toxin (data not shown).

It will be appreciated that various of the above-disclosed and other features and functions, or alternatives thereof, may be desirably combined into many other different systems or applications. Also various presently unforeseen or unanticipated alternatives, modifications, variations or improvements therein may be subsequently made by those skilled in the art, which are also intended to be encompassed by the following claims. Unless specifically recited in a claim, steps or components of claims should not be implied or imported from the specification or any other claims as to any particular order, number, position, size, shape, angle, color or material.

All references cited herein are herein incorporated by reference in entirety.

What is claimed is:

1. A method for detecting the presence of dry bacterial spores using a protein detection reagent and solid microparticles, comprising the steps of:
    a) collecting a sample suspected of comprising dry bacterial spores;
    b) contacting the solid microparticles with the collected dry bacterial spores;
    c) applying a mechanical force to the collected sample and solid microparticles sufficient to break open the spores; and,
    d) exposing the dry bacterial spores produced in step c) to at least one reagent that produces color in the presence of protein, wherein a color change indicates the presence of protein and the suspected dry bacterial spores in the sample.

2. The method of claim 1, wherein the sample is a powder.

3. The method of claim 1, wherein the sample suspected of comprising dry bacterial spores is a biowarfare agent.

4. The method of claim 3, wherein the biowarfare agent comprises *Bacillus anthracis* or *Clostridium botulinum*.

5. The method of claim 1, wherein the bacterial spores are *Bacillus* spores, *Clostridium* spores, *Bacillus cereus* or *Bacillus anthracis* spores.

6. The method of claim 1, wherein the solid microparticles are glass or zirconia/silica beads.

7. The method of claim 1, wherein the solid microparticles have a diameter from about 5 to about 500 µm.

8. The method of claim 1, wherein collecting the sample comprises using an absorbent pad or swab.

9. The method of claim 1, wherein the bacterial spores, after mechanical disruption, are contacted with the protein detection reagent.

10. The method of claim 1, wherein the dry bacterial spores are contacted with the protein detection reagent before the bacterial spores are subjected to mechanical force with the solid particles.

11. The method of claim 1, wherein the protein detection reagent is bicinchoninic acid (BCA), a mixture of phosphotungstic acid and phosphomolybdic acid, or Coomassie blue dye.

12. A method for processing dry powder for protein analysis, comprising:
    a) collecting the dry powder suspected of comprising dry bacterial spores;
    b) contacting the collected dry bacterial spores with solid microparticles;
    c) applying a mechanical force to the collected sample and solid microparticles sufficient to break open the spores; and,
    d) exposing the dry bacterial spores, produced in step c) to at least one reagent that produces color in the presence of protein, wherein a color change indicates the presence of protein and the suspected dry bacterial spores in the sample.

13. The method of claim 12, wherein the detection of protein is improved as compared to a method for processing dry powder in the absence of the solid microparticles.

14. A kit for the detecting the present of dry bacterial spores using a protein detection reagent and solid microparticles in the method of claim 1, the kit comprising:
    a) at least one aliquot of solid microparticles;
    b) a sample collection device;
    c) at least one sample tube configured for bead milling; and,
    d) a protein detection reagent.

15. The kit of claim 14, wherein the solid microparticles are glass or zirconia/silica beads.

16. The kit of claim 14, wherein the solid microparticles have a diameter from about 5 to about 500 µm.

17. The kit of claim 14, wherein the sample collection device comprises an absorbent pad, swab or a scoop.

18. The kit of claim 14, further comprising an aliquot of the solid microparticles in a microfuge tube; a mini scoop for sample collection; a pre-wetted swab with a solution of copper sulfate and a tube comprising a bicinchoninic acid solution.

19. The kit of claim 14, further comprising a battery powered vortex or instructions.

20. The kit of claim 14, wherein the protein detection reagent is bicinchoninic acid (BCA), a mixture of phosphotungstic acid and phosphomolybdic acid, or Coomassie blue dye.

* * * * *